US008278310B2

(12) United States Patent
Ly

(10) Patent No.: US 8,278,310 B2
(45) Date of Patent: Oct. 2, 2012

(54) AMINE SALTS OF A CRTH2 ANTAGONIST

(75) Inventor: Tai Wei Ly, San Diego, CA (US)

(73) Assignee: Actimis Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 12/665,705

(22) PCT Filed: Jun. 18, 2008

(86) PCT No.: PCT/US2008/007590
§ 371 (c)(1),
(2), (4) Date: Oct. 28, 2010

(87) PCT Pub. No.: WO2008/156781
PCT Pub. Date: Dec. 24, 2008

(65) Prior Publication Data
US 2011/0034482 A1    Feb. 10, 2011

Related U.S. Application Data

(60) Provisional application No. 60/936,736, filed on Jun. 21, 2007.

(51) Int. Cl.
*A01N 43/54*     (2006.01)
*C07D 239/42*    (2006.01)
*C07D 401/04*    (2006.01)
(52) U.S. Cl. ........................................ 514/256; 544/329
(58) Field of Classification Search .................... 544/329
See application file for complete search history.

(56) References Cited

U.S. PATENT DOCUMENTS

2011/0052701 A1*   3/2011   Ly et al. .................... 424/489
2011/0172250 A1*   7/2011   Ly .............................. 514/259.1

FOREIGN PATENT DOCUMENTS

WO    WO 2004/096777         11/2004
WO    WO 2004096777 A1   *   11/2004

OTHER PUBLICATIONS

L.D. Bighley et al., Salt Forms and Absorption, in 13 Encyclopedia of Pharmaceutical Technology 453 (M Swarbrick and J. Boylan eds., 1996).*
S. H. Neau, Pharmaceutical Salts, in Water-Insoluble Drug Formulation 417, 429 (R. Liu ed., CRC Press, 2008).*
S. Badaway et al., Salt Selection for Pharmaceutical Compounds, in Preformulation in Solid Dosage Form Dev. 63 (M. Adeyeye ed., 2008).*
R.J. Bastin et al., Salt Selection and Optimization Procedures for Pharmaceutical New Chemical Entities, 4 Organic Process Res. Dev. 427 (2000).*
P.L. Gould, Salt Selection for Basic Drugs, 33 Int. J. Therapeutics 201, 217 (1986).*
K. R. Morris et al., An Integrated Approach to the Selection of Optimal Salt Form for a New Drug Candidate, 105 Int'l. J. Pharm. 209 (1994).*

K. Chow et al., Engineering of Pharmaceutical Materials: an Industrial Perspective, 97 J. Pharmaceutical Sciences, 2855 (2008).*
Nagata et al., "Selective expression of a novel surface molecule by human Th2 cells in vivo," *J. Immunol.* 162, 1278-1286 (1999).
Hirai et al., "Prostaglandin D2 selectively induces chemotaxis in T helper type 2 cells, eosinophils, and basophils via seven-transmembrane receptor CRTH2," *J. Exp. Med.* 193, 255-261 (2001).
Gervais et al., "Selective modulation of chemokinesis, degranulation, and apoptosis in eosinophils through the PGD2 receptors CRTH2 and DP," *J. Allergy Clin. Immunol.* 108, 982-988 (2001).
Cosmi et al., "CRTH2 is the most reliable marker for the detection of circulating human type 2 Th and type 2 T cytotoxic cells in health and disease," *Eur. J. Immunol.*, 30, 2972-2979 (2000).
Iwazaki et al., "Association of a new-type prostaglandin D2 receptor CRTH2 with circulating T helper 2 cells in patients with atopic dermatitis," *J. Investigative Dermatology* 119, 609-616 (2002).
Fujitani et al., "Pronounced eosinophilic lung inflammation and Th2 cytokine release in human lipocalin-type prostaglandin D synthase transgenic mice," *J. Immunol.*, 168, 443-449 (2002).
Sugimoto et al., "An orally bioavailable small molecule antagonist of CRTH2, ramatroban (BAY u3405), inhibits prostaglandin $D_2$-induced eosinophil migration in vitro," *J. Pharm. Exp. Therap.*, 305, 347-352 (2003).
Sugimoto et al., "CRTH2-Specific binding characteristics of [$^3$H]ramatroban and its effects on $PGD_2$-, 15-deoxy-$\Delta^{12,\ 14}$-$PGJ_2$- and indomethacin-induced agonist responses," *Eur. J. Pharmacol.*, 524, 30-37 (2005).
Narumiya et al., "Prostanoid receptors: structures, properties and functions," *Physiol. Revs.*, 79, 1193-1226 (1999).
Hamilos et al., "Eosinophil infiltration in nonallergic chronic hyperplastic sinusitis with nasal polyposis (CHS/NP) is associated with endothelial VCAM-1 upregulation and expression of TNF-α," *Am. J. Resp. Cell Mol. Biol.*, 15, 443-450 (1996).
Misumori, "Recent progress in work on PGD2 antagonists for drugs targeting allergic diseases," *Curr. Pharm. Design*, 10, 3533-3538 (2004).
Nagata et al., "CRTH2, An orphan receptor of T-helper-2 cells, is expressed on basophils and eosinophils and responds to mast-cell-derived factor(s)," *FEBS Lett.*, 459, 195-199 (1999).
Shichijo et al., "Chemoattractant receptor-homologous molecule expressed on Th2 cells activation in vivo increases blood leukocyte counts and its blockade abrogates 13,14-dihydro-15-keto prostaglandin D2-induced eosinophilia in rats," *J. Pharm. Exp. Therap.*, 307, 518-525 (2003).
Cheng et al., "Relationship between the inhibition constant Ki and the concentration of inhibitor which causes 50% inhibition ($IC_{50}$) of an enzymatic reaction," *Biochem. Pharmacol.*, 22, 3099-3108 (1973).
Grynkiewicz et al., "A new generation of $Ca^{2+}$ indicators with greatly improved fluorescence properties," *J. Biol. Chem.*, 260, 3440-3450 (1985).
Ly and Bacon, "Small-molecule CRTH2 antagonists for the treatment of allergic inflammation: an overview," *Expert Opin. Investig. Drugs* 2005. 14, 769-773.

(Continued)

*Primary Examiner* — James O Wilson
*Assistant Examiner* — Alexander R Pagano
(74) *Attorney, Agent, or Firm* — Jones Day

(57) ABSTRACT

Provided are amine salts of {4,6-bis(dimethylamino)-2-(4-(4-(trifluoromethyl)benzamido)benzyl)pyrimidin-5-yl}-acetic acid, processes for their preparation, pharmaceutical compositions containing them, and their use for treating, preventing, or ameliorating one or more symptoms of a CRTH2-mediated disorder or disease.

39 Claims, 20 Drawing Sheets

OTHER PUBLICATIONS

Peterson et al., "Expanding the scope of crystal form evaluation in pharmaceutical science," J. Pharm. Pharmaceut. Sci., 2006, 9, 317-326.

Bernstein, "Crystal structure prediction and polymorphism," ACA Transactions 2004, 39, 14-23.

* cited by examiner

US 8,278,310 B2

AMINE SALTS OF A CRTH2 ANTAGONIST

CROSS REFERENCE TO RELATED APPLICATIONS

This application is a 371 of PCT/US2008/007590, filed Jun. 18, 2008, which claims priority to U.S. Provisional No. 60/936,736, filed Jun. 21, 2007, which is incorporated by reference in its entirety.

FIELD

Provided herein are amine salts of {4,6-bis(dimethylamino)-2-(4-(4-(trifluoromethyl)benzamido)benzyl)pyrimidin-5-yl}acetic acid, processes of preparation, and pharmaceutical compositions thereof. Also provided are methods of their use for treating, preventing, or ameliorating one or more symptoms of a CRTH2-mediated disorder or disease.

BACKGROUND

CRTH2 is a G protein-coupled chemoattractant receptor expressed on Th2 cells, eosinophils, and basophils (Nagata et al., *J. Immunol.* 1999, 162, 1278-1286; Hirai et al., *J. Exp. Med.*, 2001, 193, 255-261). Prostaglandin $D_2$ ($PGD_2$), the major inflammatory mediator produced from mast cells, is a natural ligand for CRTH2. Recently, it has been shown that the activation of CRTH2 by $PGD_2$ induces the migration and activation of Th2 cells and eosinophils, suggesting that CRTH2 may play a pro-inflammatory role in allergic diseases (Hirai et al., *J. Exp. Med.* 2001, 193, 255-261; Gervais et al., *J. Allergy Clin. Immunol.* 2001, 108, 982-988). It has also been shown that, in atopic dermatitis patients, there is an increase in circulating T cells expressing CRTH2, which correlates with the severity of the disease (Cosmi et al., *Eur. J. Immunol.*, 2000, 30, 2972-2979; Iwazaki et al., *J. Investigative Dermatology*, 2002, 119, 609-616). The role of $PGD_2$ in the initiation and maintenance of allergic inflammation has further been demonstrated in mouse models of asthma by showing that overproduction of $PGD_2$ in vivo by $PGD_2$ synthase exacerbates airway inflammation (Fujitani et al., *J. Immunol.* 2002, 168, 443-449). Therefore, CRTH2 antagonists are potentially useful for the treatment of CRTH2-mediated disorders or diseases, such as allergic rhinitis, allergic asthma, bronchoconstriction, atopic dermatitis, or systemic inflammatory disorders.

SUMMARY OF THE DISCLOSURE

Provided are amine salts of {4,6-bis(dimethyl-amino)-2-(4-(4-(trifluoro-methyl)benzamido)benzyl)pyrimidin-5-yl}acetic acid, which has Formula I:

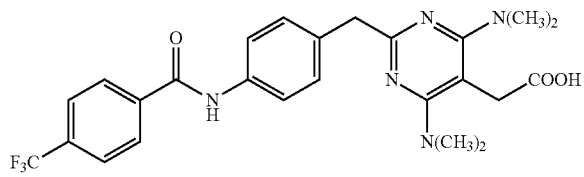

(I)

or pharmaceutically acceptable hydrates and solvates thereof. The compound of Formula I has been identified as a CRTH2 antagonist (WO 2004/0022218).

In one embodiment, the amine salts comprising the acid of Formula I and a pharmaceutical acceptable amine are crystalline.

In another embodiment, the amine salts comprise the acid of Formula I and a pharmaceutically acceptable amine, except ethanolamine, triethylamine, and tris(hydroxy-methyl)aminomethane.

In yet another embodiment, the amine salts of {4,6-bis(dimethylamino)-2-(4-(4-(trifluoromethyl)benzamido)benzyl)pyrimidin-5-yl}acetic acid are diamine salts, which each comprise about two molar equivalents of the acid of Formula I and about one molar equivalent of the diamine.

In yet another embodiment, the diamine salts of {4,6-bis(dimethylamino)-2-(4-(4-(trifluoromethyl)benzamido)benzyl)pyrimidin-5-yl}acetic acid are crystalline.

In yet another embodiment, the amine salts of {4,6-bis(dimethylamino)-2-(4-(4-(trifluoromethyl)benzamido)benzyl)pyrimidin-5-yl}acetic acid are monoamine salts, which each comprise about one molar equivalent of the acid of Formula I and about one molar equivalent of the monoamine.

In still another embodiment, the monoamine salts of {4,6-bis(dimethylamino)-2-(4-(4-(trifluoromethyl)benzamido)benzyl)pyrimidin-5-yl}acetic acid are crystalline.

Also provided is a process for preparing an amine salt of 4,6-bis(dimethyl-amino)-2-(4-(4-(trifluoromethyl)benzamido)benzyl)pyrimidin-5-yl}acetic acid, or a pharmaceutically acceptable hydrate or solvate thereof.

In one embodiment, the process comprises reacting {4,6-bis(dimethylamino)-2-(4-(4-(trifluoromethyl)benzamido)benzyl)pyrimidin-5-yl}acetic acid with an amine in a solvent at a first predetermined temperature.

In another embodiment, the process further comprises precipitating the amine salt at a second predetermined temperature.

In yet another embodiment, the process comprises the steps of: (a) generating the amine salt by reacting {4,6-bis(dimethylamino)-2-(4-(4-(trifluoromethyl)benzamido)-benzyl)pyrimidin-5-yl}acetic acid with an amine in a solvent at a first predetermined temperature; and (b) precipitating the amine salt at a second predetermined temperature.

Further provided is a pharmaceutical composition, comprising an amine salt of {4,6-bis(dimethylamino)-2-(4-(4-(trifluoromethyl)benzamido)benzyl)-pyrimidin-5-yl}acetic acid, or a pharmaceutically acceptable hydrate or solvate thereof, and one or more pharmaceutically acceptable carriers or excipients.

Additionally, provided is a method for treating, preventing, or ameliorating one or more symptoms of a CRTH2-mediated disorder or disease, which comprises administering to a mammal a therapeutically effective amount of an amine salt of {4,6-bis(dimethylamino)-2-(4-(4-(trifluoromethyl)benzamido)benzyl)pyrimidin-5-yl}acetic acid, or a pharmaceutically acceptable hydrate or solvate thereof.

DETAILED DESCRIPTION

Figure 1:
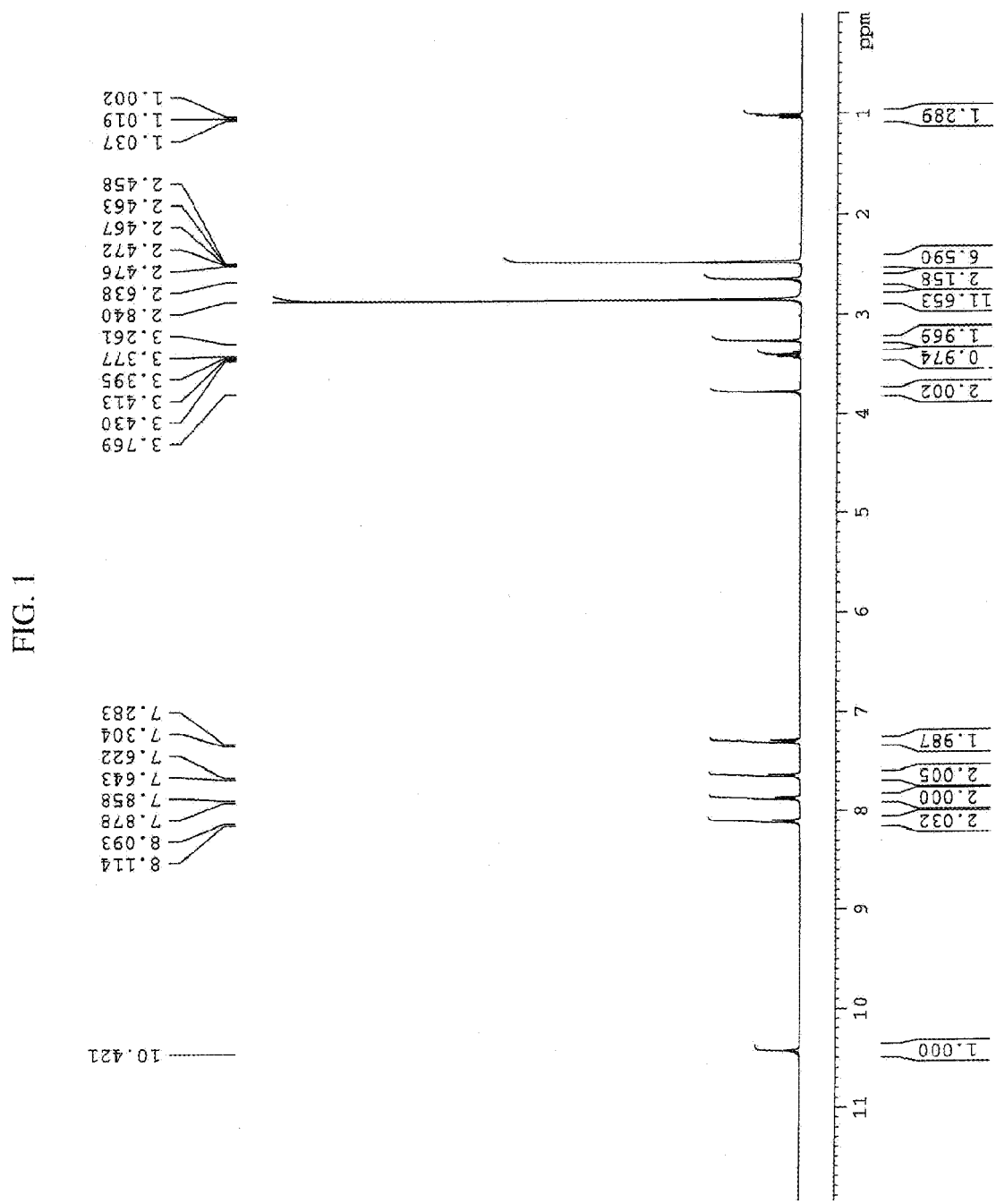
FIG. 1 depicts a proton nuclear magnetic resonance ($^1$H NMR) spectrum of the crystalline ethylenediamine salt of {4,6-bis(dimethylamino)-2-(4-(4-(trifluoromethyl)-benzamido)benzyl)-pyrimidin-5-yl}acetic acid of Formula I.

To facilitate understanding of the disclosure set forth herein, a number of terms are defined below.

As used herein, the singular forms "a," "an," and "the" may refer to plural articles unless specifically stated otherwise. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term herein, those in this section prevail unless stated otherwise.

The term "anti-solvent" refers to a liquid that is added to a solvent to reduce the solubility of a compound in that solvent, resulting in precipitation of the compound.

The term "subject" refers to an animal, including, but not limited to, a primate (e.g., human), cow, sheep, goat, horse, dog, cat, rabbit, rat, or mouse. Typically, the terms "subject" and "patient" are used interchangeably herein in reference, for example, to a mammalian subject, particularly a human subject.

The terms "treat," "treating," and "treatment" are meant to include alleviating or abrogating a disorder or disease, or one or more of the symptoms associated with the disorder or disease; or alleviating or eradicating the cause(s) of the disorder or disease itself.

The terms "prevent," "preventing," and "prevention" refer to a method of delaying or precluding the onset of a disease and/or its attendant symptoms, barring a subject from acquiring a disease, or reducing a subject's risk of acquiring a disease.

The term "therapeutically effective amount" refers to the amount of a compound that, when administered, is sufficient to prevent development of, or alleviate to some extent, one or more of the symptoms of a disease, condition, or disorder being treated. The term "therapeutically effective amount" also refers to the amount of a compound that will elicit the biological or medical response of a tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "CRTH2" refers to a CRTH2 receptor protein or variant thereof, which is capable of mediating a cellular response to $PGD_2$ in vitro or in vivo. CRTH2 variants include proteins substantially homologous to a native CRTH2, i.e., proteins having one or more naturally or non-naturally occurring amino acid deletions, insertions or substitutions (e.g., CRTH2 derivatives, homologs and fragments), as compared to the amino acid sequence of a native CRTH2. The amino acid sequence of a CRTH2 variant is at least about 80% identical, at least about 90% identical, or at least about 95% identical to a native CRTH2.

The term "other $PGD_2$ receptor" refers to a prostanoid receptor protein other than CRTH2, or variant thereof, which is capable of mediating a cellular response to $PGD_2$ in vivo or in vitro. "Other $PGD_2$ receptor" may be selective for $PGD_2$, e.g., DP, or other one or more other prostanoids. "Other $PGD_2$ receptor" variants include proteins substantially homologous to a corresponding native prostanoid receptor other than CRTH2, i.e., proteins having one or more naturally or non-naturally occurring amino acid deletions, insertions, or substitutions (e.g., derivatives, homologs, and fragments of a native prostanoid receptor other than CRTH2). The amino acid sequence of a native "other $PGD_2$ receptor" variants is at least about 80% identical, at least about 90% identical, or at least about 95% identical to the corresponding native "other $PGD_2$ receptor".

The term "CRTH2 antagonist" refers to a compound that, e.g., partially or totally blocks, decreases, prevents, inhibits, or downregulates CRTH2 activity and/or the activity of one or more other PGD$_2$ receptors. The term "CRTH2 antagonist" also refers to a compound that binds to, delays the activation of, inactivates, or desensitizes CRTH2 or one or more other PGD$_2$ receptors. A CRTH2 antagonist may act by interfering with the interaction of PGD$_2$ with CRTH2 or one or more other PGD$_2$ receptors.

The terms "CRTH2-mediated disorder or disease" and "a condition, disorder or disease mediated by CRTH2" refer to a condition, disorder, or disease characterized by inappropriate, e.g., less than or greater than normal, CRTH2 activity. Inappropriate CRTH2 functional activity might arise as the result of CRTH2 expression in cells which normally do not express CRTH2, increased CRTH2 expression or degree of intracellular activation, leading to, e.g., inflammatory and immune-related disorders or diseases; or decreased CRTH2 expression. A CRTH2-mediated condition, disorder or disease may be completely or partially mediated by inappropriate CRTH2 activity. In particularly, a CRTH2-mediated condition, disorder or disease is one in which modulation of CRTH2 or one or more other PGD$_2$ receptors results in some effect on the underlying condition or disorder, e.g., a CRTH2 antagonist or agonist results in some improvement in at least some of patients being treated.

Amine Salts

Provided herein are amine salts of {4,6-bis(dimethylamino)-2-(4-(4-(trifluoromethyl)benzamido)benzyl)pyrimidin-5-yl}acetic acid, and solvates thereof; and processes for their preparation. Also provided are pharmaceutical compositions of these amine salts or solvates thereof, and methods of their use for treating, preventing, or ameliorating one or more symptoms of a CRTH2-mediated disorder or disease.

In accordance with one embodiment, a pharmaceutically acceptable amine salt of {4,6-bis(dimethylamino)-2-(4-(4-(trifluoromethyl)benzamido)benzyl)-pyrimidin-5-yl}acetic acid is provided, which comprises the acid of Formula I and a pharmaceutically acceptable amine. In another embodiment, provided is a solvate of a pharmaceutically acceptable crystalline amine salt of {4,6-bis(dimethylamino)-2-(4-(4-(trifluoromethyl)benzamido)benzyl)-pyrimidin-5-yl}acetic acid, which comprises the acid of Formula I, a pharmaceutically acceptable amine, and a solvent.

In certain embodiments, the molar ratio of the acid of Formula I versus the amine in an amine salt or a solvate thereof is from about 0.5 to about 10, from 0.5 to about 5, from about 0.5 to about 3, from about 0.5 to about 2, or from about 0.8 to about 1.2, or about 1.

In certain embodiments, the molar ratio of the acid of Formula I versus the solvent in a solvate of an amine salt provided herein is from about 0.1 to about 2, from about 0.2 to about 1, or from about 0.3 to about 0.5, or about 0.1, about 0.2, about 0.3, about 0.4, about 0.5, about 0.6, about 0.7, about 0.8, about 0.9, or about 1.

Suitable amines for use in the amine salts or solvates thereof as provided herein include, but are not limited to, primary amines, including methylamine, ethylamine, ethanolamine, tris(hydroxymethyl)aminomethane, and ethylenediamine; secondary amines, including dimethylamine, diethylamine, diisopropylamine, dibutylamine, di-sec-butylamine, dicyclohexylamine, diethanolamine, meglumine, pyrrolidine, piperidine, piperazine, and benzathine; tertiary amines, including trimethylamine, triethylamine, triethanolamine, and 1-(2-hydroxyethyl)-pyrrolidine; quaternary ammoniums, including choline, tetra-methylammonium, and tetra-ethylammonium. For a review on additional amines, see "*Handbook of Pharmaceutical Salts: Properties, Selection, and Use*" by Stahl and Wermuth, Wiley-VCH, 2002.

In one embodiment, the pharmaceutical acceptable amine is a diamine. The pharmaceutically acceptable diamine has first and second amino groups, which each are independently a primary, secondary, or tertiary amino group, or quaternary ammonium group. Suitable diamines for use in the diamine salt include, but are not limited to, ethylenediamine, piperazine, and benzathine. The diamine salt of {4,6-bis(dimethylamino)-2-(4-(4-(trifluoromethyl)benzamido)benzyl)-pyrimidin-5-yl}acetic acid comprises from about 1 to about 3, from about 1.5 to about 2.5, from about 1.75 to about 2.25, or about 2 molar equivalents of the acid of Formula I for one molar equivalent of the diamine.

In one group of the diamine salts of this embodiment, the first amino group of the diamine is a primary amino group, and the second amino group is independently a primary, secondary, or tertiary amino group, or quaternary ammonium. In another group of the diamine salts, the first amino group is independently a secondary amino group, and the second amino group is a primary, secondary, or tertiary amino group, or quaternary ammonium. In yet another group of the diamine salts, the first amino group is independently a tertiary amino group, and the second amino group is a primary, secondary, or tertiary amino group, or quaternary ammonium. In yet another group of the diamine salts, the first amino group is a quaternary ammonium, and the second amino group is independently a primary, secondary, or tertiary amino group, or quaternary ammonium.

In yet another embodiment, the pharmaceutical acceptable amine is a diamine with two primary amino groups. The primary diamine salt of the acid of Formula I comprises from about 1 to about 3, from about 1.5 to about 2.5, from about 1.75 to about 2.25, or about 2 molar equivalents of the acid of Formula I for one molar equivalent of the primary diamine.

In yet another embodiment, the primary diamine is ethylenediamine. The ethylenediamine salt of {4,6-bis(dimethylamino)-2-(4-(4-(trifluoromethyl)benzamido)-benzyl)pyrimidin-5-yl}acetic acid comprises about two molar equivalents of the acid of Formula I and about one molar equivalent of ethylenediamine, as estimated based on its $^1$H NMR spectrum (FIG. 1).

Figure 2:
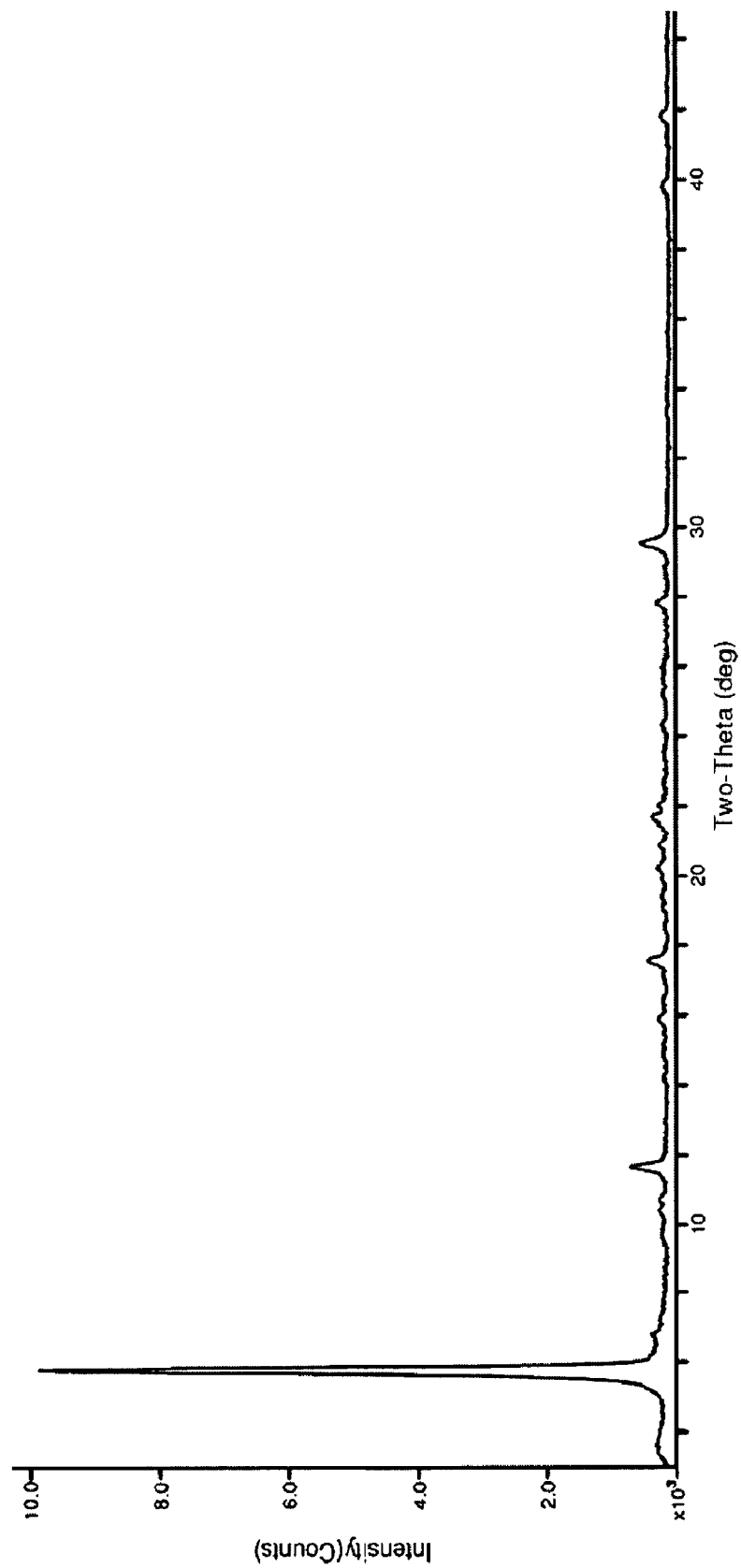
FIG. 2 depicts an X-ray powder (XRP) diffractogram of the crystalline ethylenediamine salt of the acid of Formula I.
Figure 3:
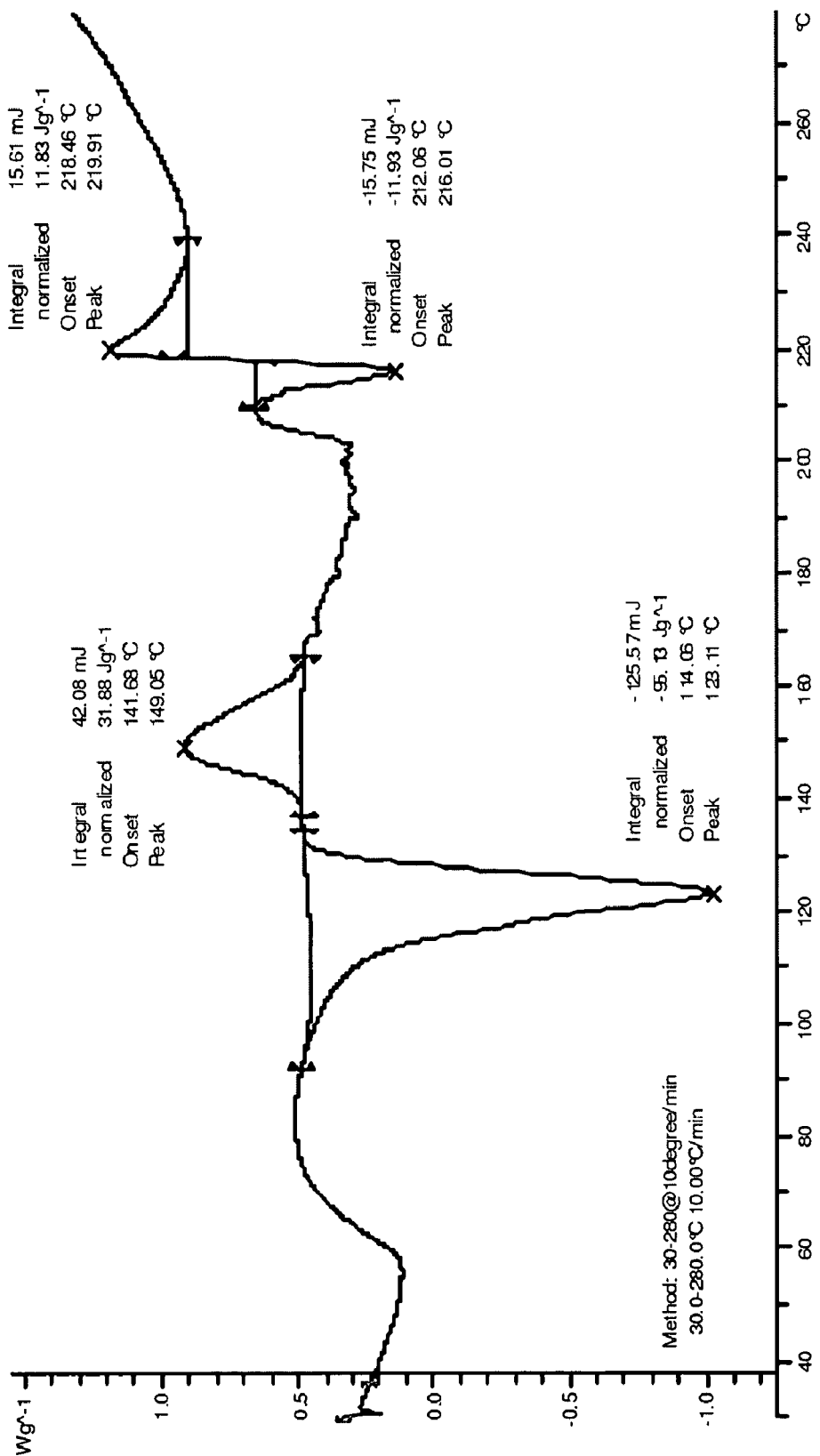
FIG. 3 depicts a differential scanning calorimetric (DSC) thermogram of the crystalline ethylenediamine salt of the acid of Formula I.

In yet another embodiment, the ethylenediamine salt of the acid of Formula I is crystalline. The crystalline ethylenediamine salt has an XRP diffraction pattern substantially as shown in FIG. 2. Particularly, the crystalline ethylenediamine salt has a characteristic XRP diffraction peak at a two-theta angle of approximately 5.9°. Furthermore, the crystalline ethylenediamine salt has a DSC thermogram substantially as shown in FIG. 3. The crystalline ethylenediamine salt has an endotherm with a peak temperature of about 123° C. and an onset temperature of 114° C., or with a peak temperature of about 216° C. and an onset temperature of about 212° C. Alternatively, the crystalline ethylenediamine salt has endotherms with a peak temperature of about 123° C. and an onset temperature of 114° C., and a peak temperature of about 216° C. and an onset temperature of about 212° C.

In yet another embodiment, provided herein is a crystalline ethylenediamine salt of the acid of Formula I. The solvate has an XRP diffraction pattern substantially as shown in FIG. 2. Particularly, the solvate has a characteristic XRP diffraction peak at a two-theta angle of approximately 5.9°. Furthermore, the solvate has a DSC thermogram substantially as shown in FIG. 3. The solvate has an endotherm with a peak temperature of about 123° C. and an onset temperature of 114° C., or with a peak temperature of about 216° C. and an onset temperature of about 212° C. Alternatively, the solvate has endotherms with a peak temperature of about 123° C. and an onset temperature of 114° C., and a peak temperature of about 216° C. and an onset temperature of about 212° C.

In one embodiment, the solvate shows from about 1% to about 10%, including, but not limited to, about 1%, about 2%, about 3%, about 4%, about 5%, about 6%, about 7%, about 8%, about 9%, and about 10% weight loss between 125° C. to 150° C. In another embodiment, the solvate shows from 2%, about 3%, about 4%, or about 5% weight loss between 125° C. to 150° C.

In one embodiment, the solvate contains from about 0.1 to about 2, from about 0.2 to about 1, or from about 0.3 to about 0.5; or about 0.1, about 0.2, about 0.3, about 0.4, about 0.5, about 0.6, about 0.7, about 0.8, about 0.9, or about 1 molar equivalent of the solvent for every molar equivalent of the amine salt. In another embodiment, the solvate contains from about 0.3 to about 0.5 molar equivalent of the solvent for every molar equivalent of the amine salt. In yet another embodiment, the solvate contains about 0.3 molar equivalent of the solvent for every molar equivalent of the amine salt. In yet another embodiment, the solvate contains about 0.4 molar equivalent of the solvent for every molar equivalent of the amine salt. In still another embodiment, the solvate contains about 0.5 molar equivalent of the solvent for every molar equivalent of the amine salt.

In one embodiment, the solvent in the solvate is an alcohol, including, but not limited to, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol. In another embodiment, the solvent is ethanol.

In yet another embodiment, the pharmaceutical acceptable amine is a diamine with two secondary amino groups. The secondary diamine salt of the acid of Formula I comprises from about 1 to about 3, from about 1.5 to about 2.5, from about 1.75 to about 2.25, or about 2 molar equivalents of the acid of Formula I for one molar equivalent of the secondary diamine.

Figure 6:
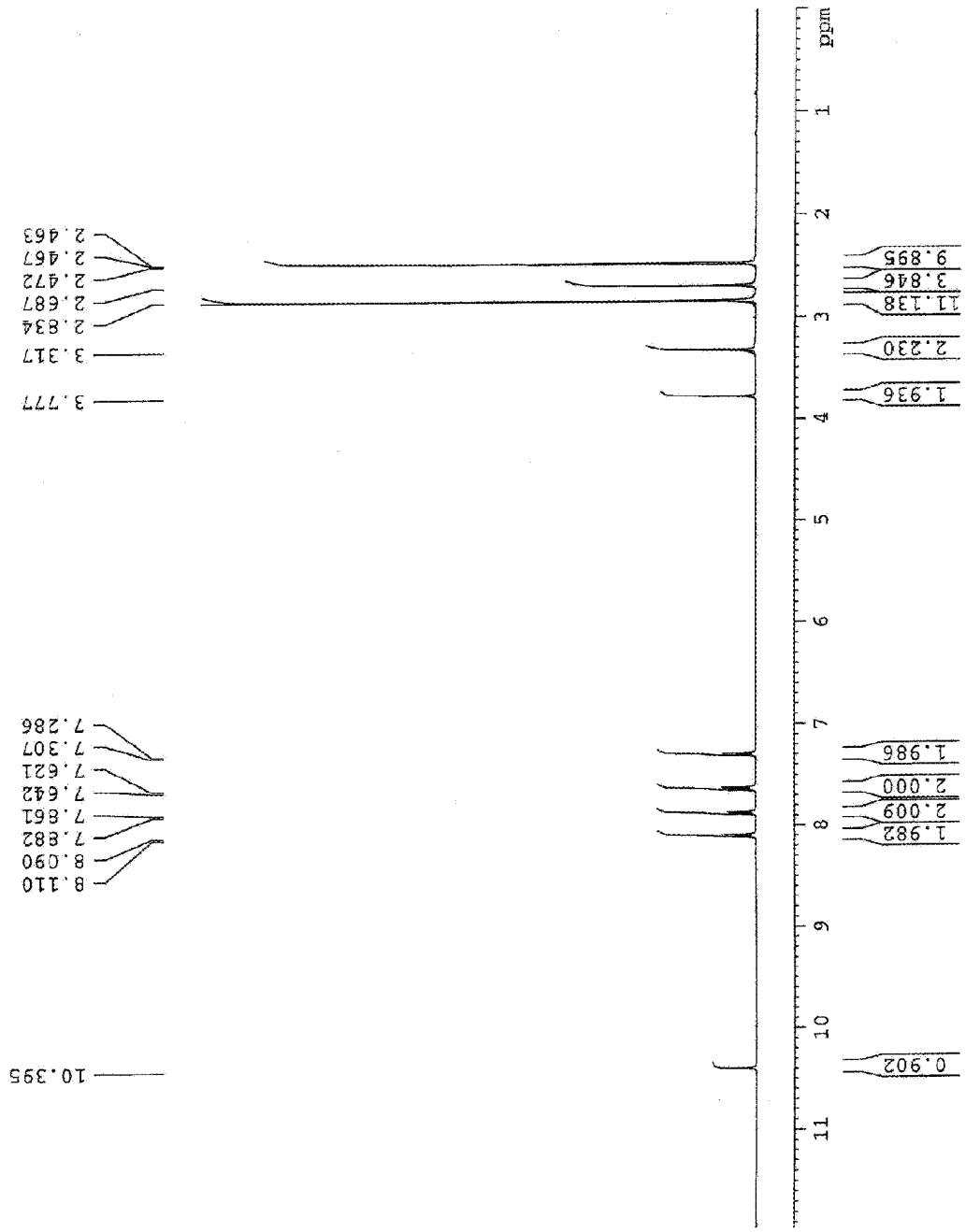
FIG. 6 depicts a $^1$H NMR spectrum of the crystalline piperazine salt of the acid of Formula I.

In yet another embodiment, the secondary diamine is piperazine. The piperazine salt of {4,6-bis(dimethylamino)-2-(4-(4-(trifluoromethyl)benzamido)benzyl)-pyrimidin-5-yl}acetic acid comprises about two molar equivalents of the acid of Formula I and about one molar equivalent of piperazine, as estimated based on its $^1$H NMR spectrum (FIG. 6).

Figure 7:
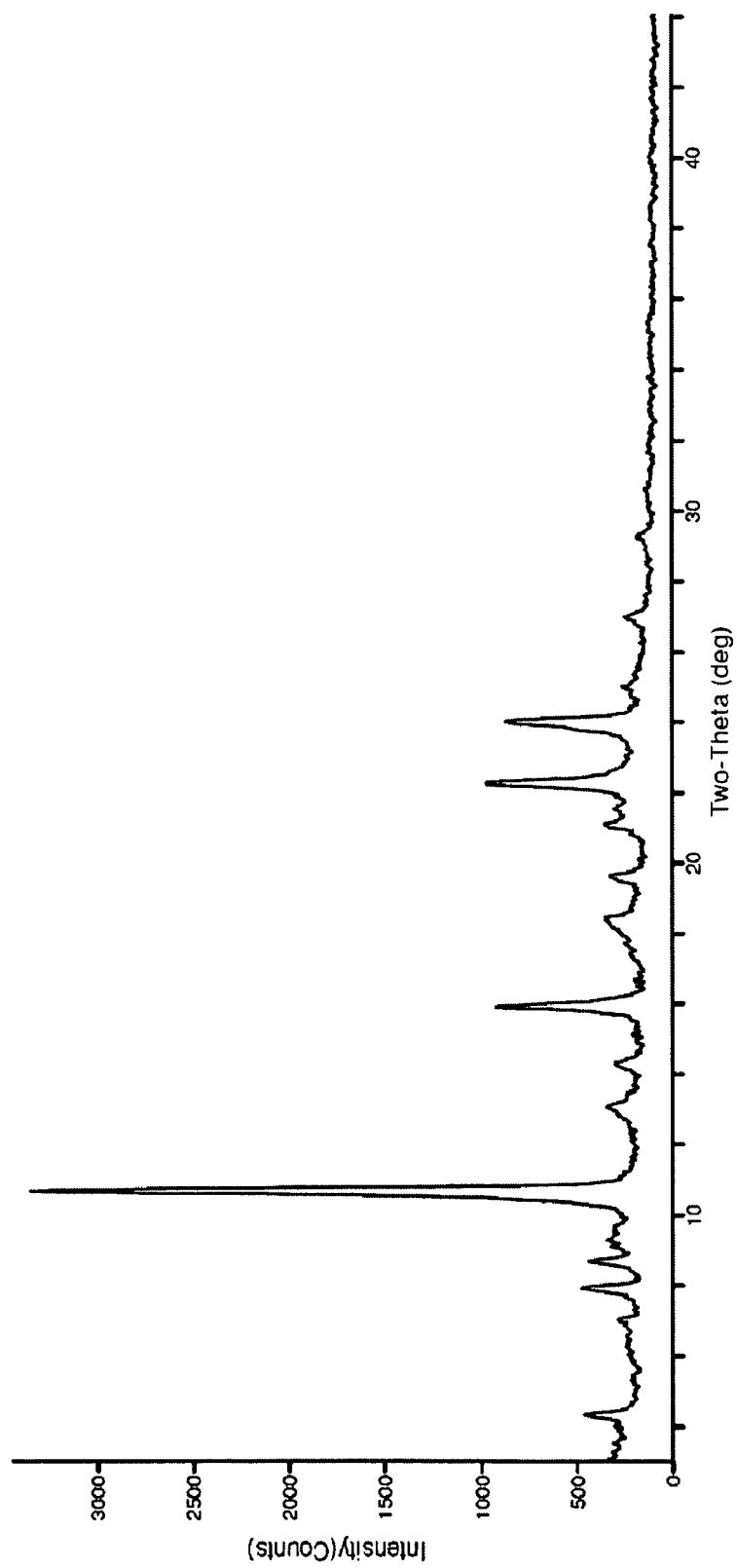
FIG. 7 depicts an XRP diffractogram of the crystalline piperazine salt of the acid of Formula I.
Figure 8:
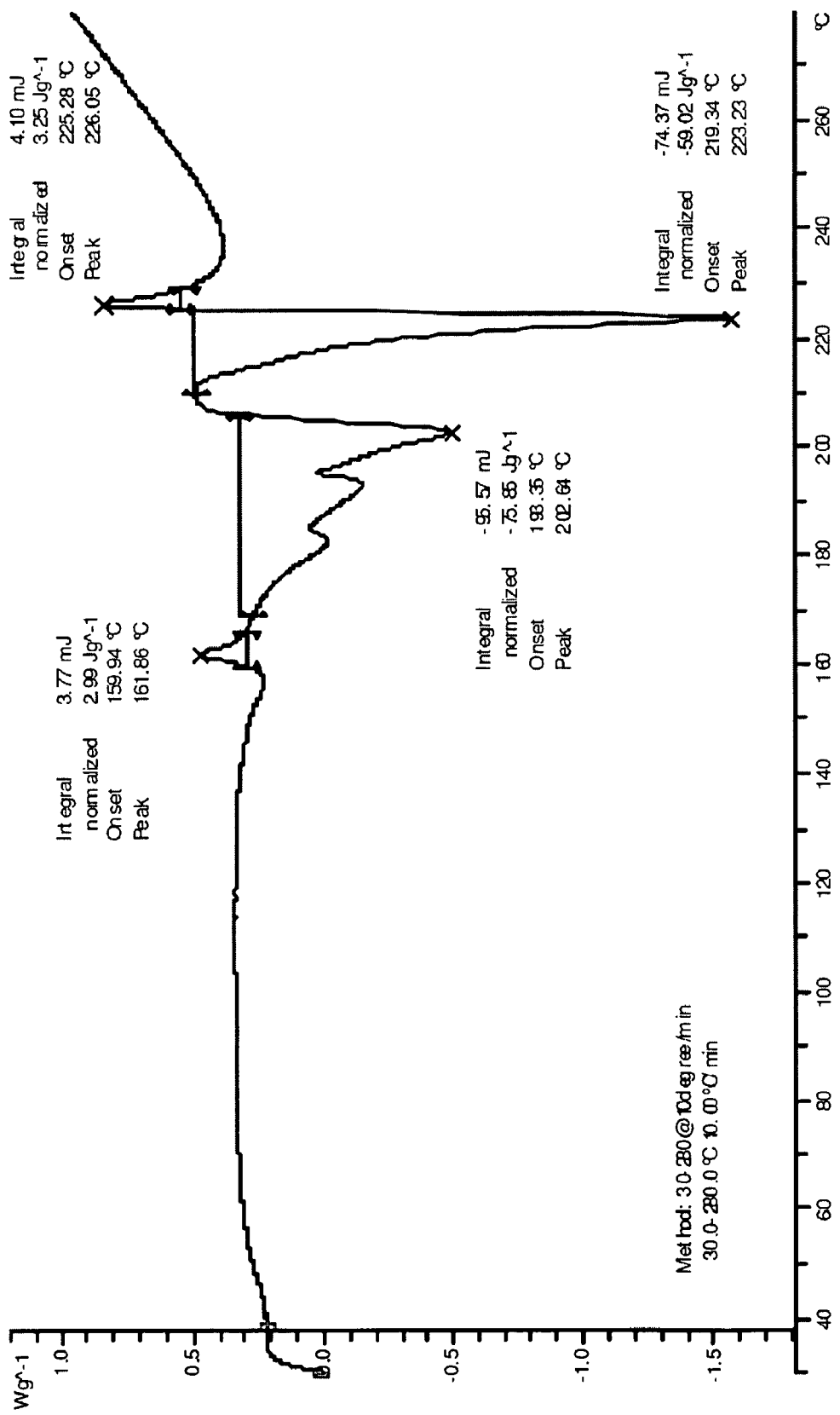
FIG. 8 depicts a DSC thermogram of the crystalline piperazine salt of the acid of Formula I.

In yet another embodiment, the piperazine salt is crystalline. The crystalline piperazine salt has an XRP diffraction pattern substantially as shown in FIG. 7. In one embodiment, the piperazine salt has characteristic XRP diffraction peaks at two-theta angles of approximately 10.7, 15.9, 22.3, and 24.0°. In another embodiment, the piperazine salt has a characteristic XRP diffraction peak at a two-theta angle of approximately 10.7, 15.9, 22.3, or 24.0°. In yet another embodiment, the crystalline piperazine salt has a DSC thermogram substantially as shown in FIG. 8. In still another embodiment, the crystalline piperazine salt has an endotherm with a peak temperature of about 203° C. and an onset temperature of about 197° C., or with a peak temperature of about 223° C. and an onset temperature of about 219° C. In an alternative embodiment, the crystalline piperazine salt has endotherms with a peak temperature of about 203° C. and an onset temperature of about 197° C., and a peak temperature of about 223° C. and an onset temperature of about 219° C.

Figure 11:
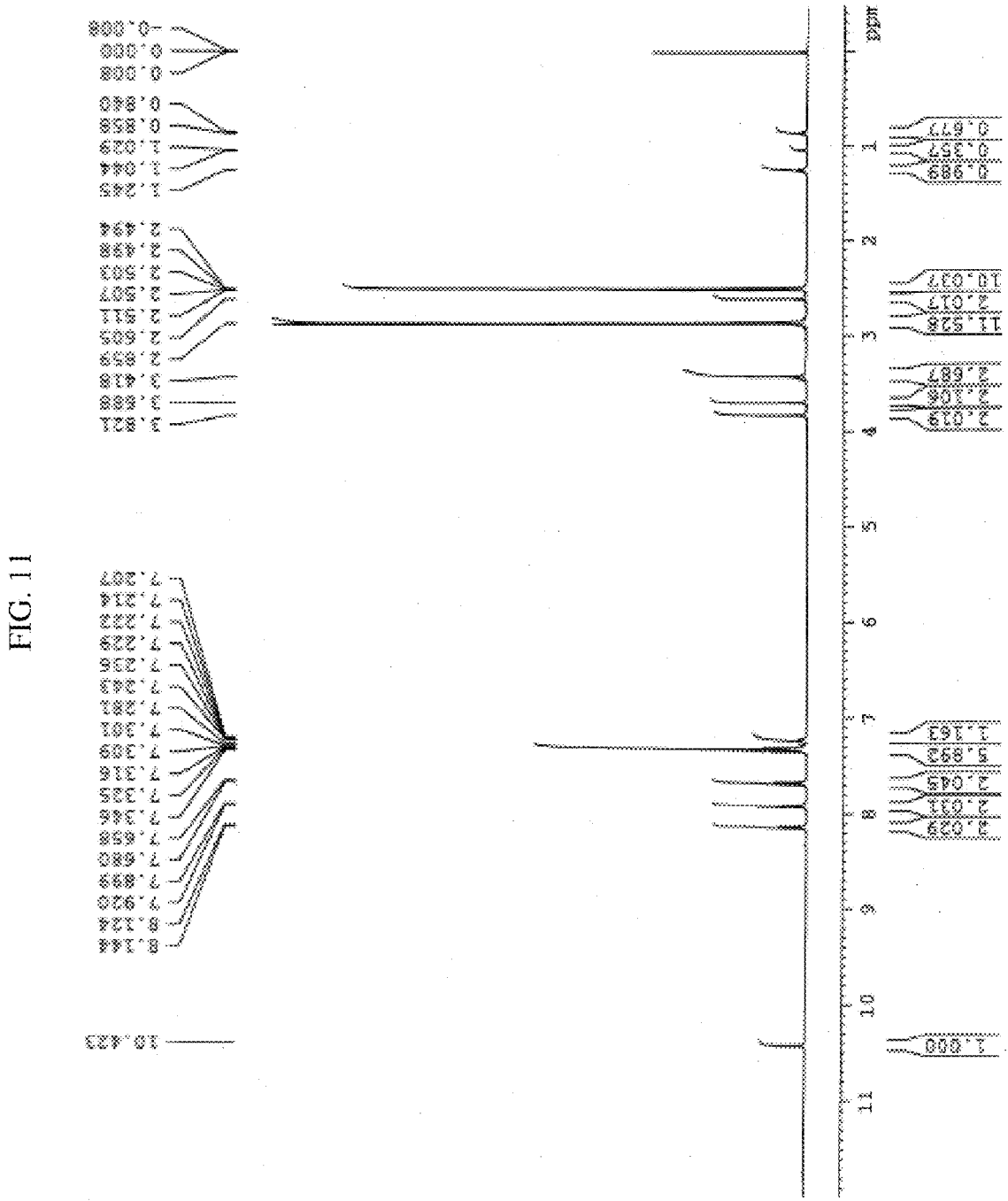
FIG. 11 depicts a $^1$H NMR spectrum of the crystalline benzathine salt of the acid of Formula I.

In yet another embodiment, the secondary diamine is benzathine. The benzathine salt of {4,6-bis(dimethylamino)-2-(4-(4-(trifluoromethyl)benzamido)benzyl)-pyrimidin-5-yl}acetic acid comprises about two molar equivalents of the acid of Formula (I) and about one molar equivalent of benzathine, as estimated based on its $^1$H NMR spectrum (FIG. 11).

Figure 12:
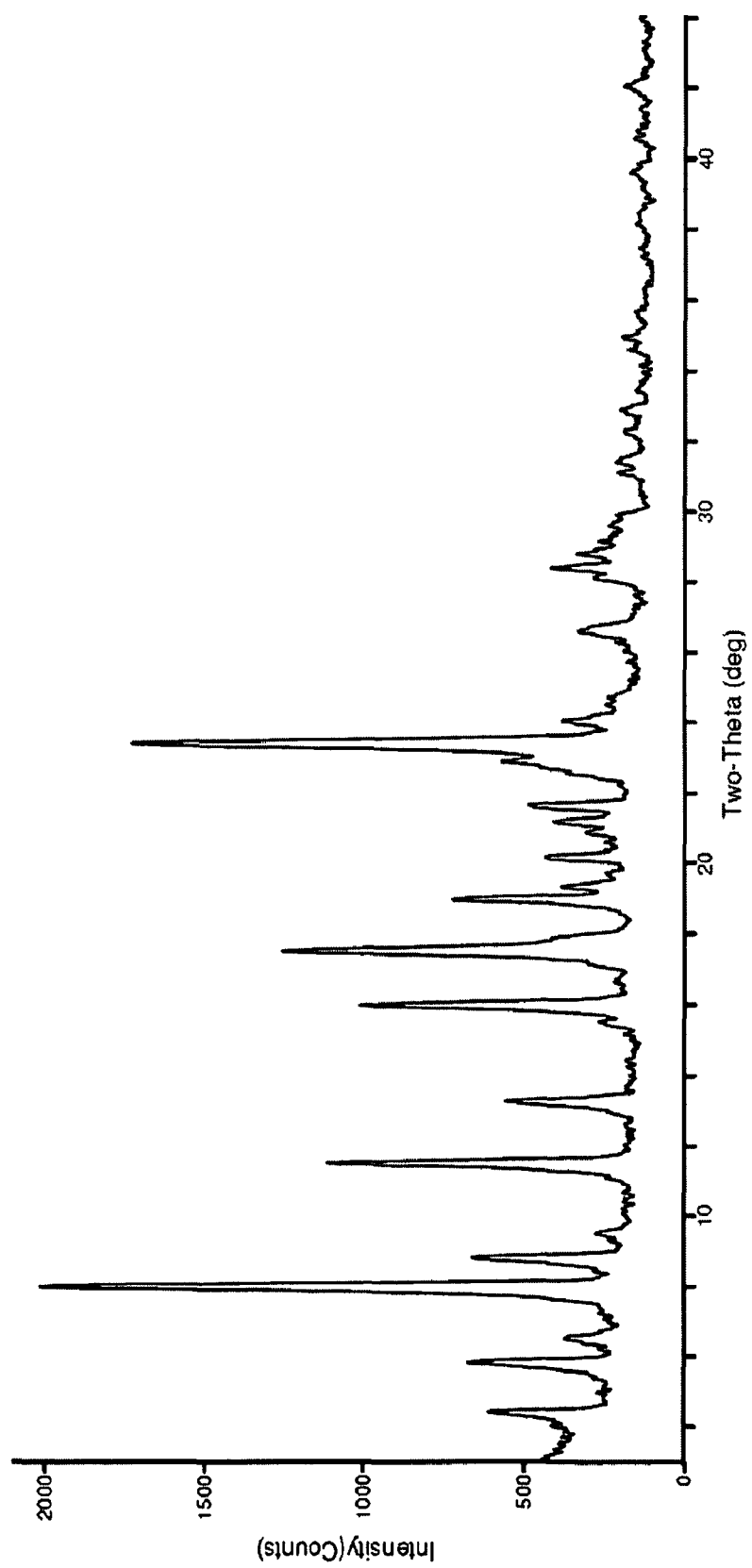
FIG. 12 depicts an XRP diffractogram of the crystalline benzathine salt of the acid of Formula I.
Figure 13:
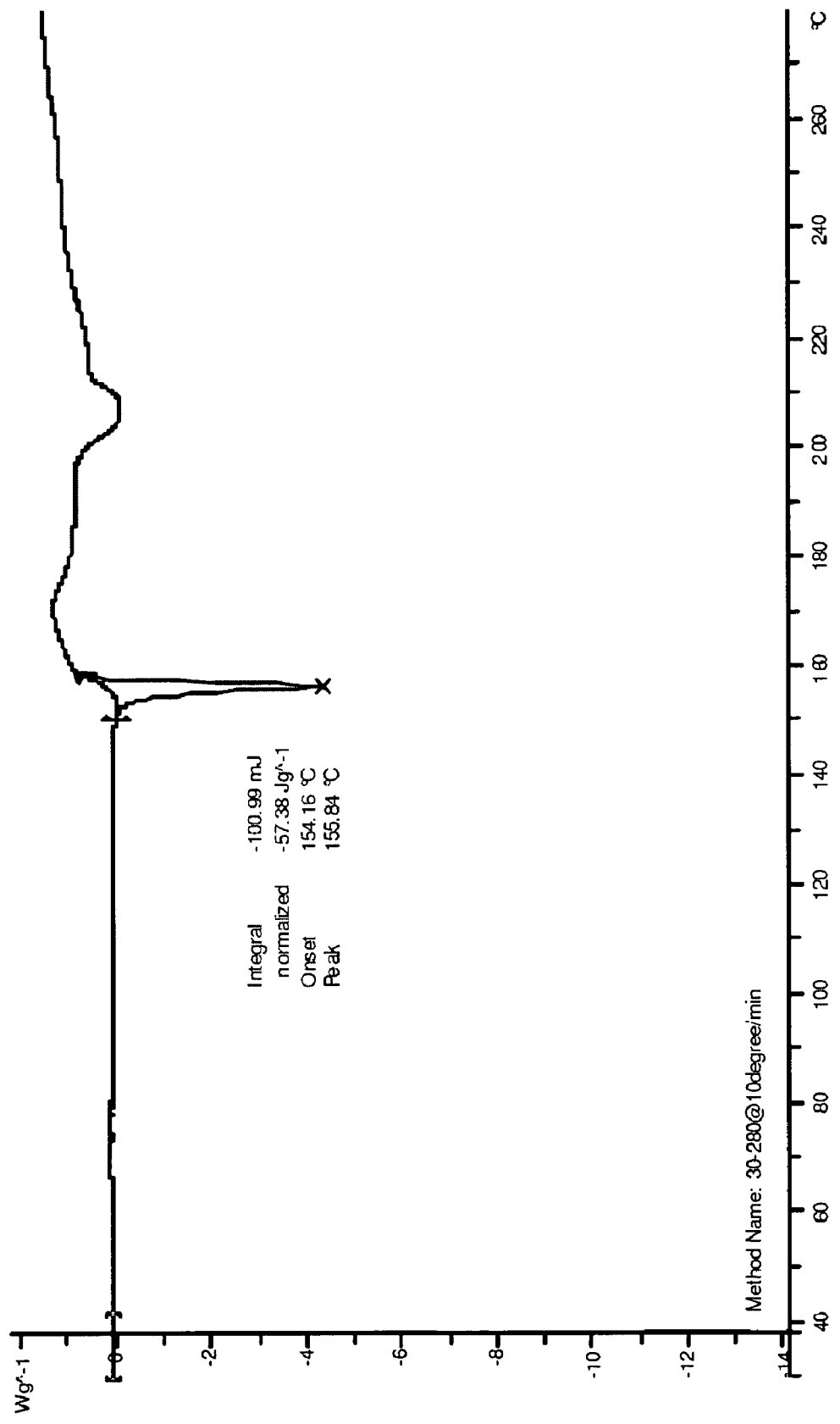
FIG. 13 depicts a DSC thermogram of the crystalline benzathine salt of the acid of Formula I.

In yet another embodiment, the benzathine salt is crystalline, which has an XRP diffraction pattern substantially as shown in FIG. 12. In one embodiment, the benzathine salt has characteristic XRP diffraction peaks at two-theta angles of approximately 8.0, 11.5, 16.0, 17.5, and 23.4°. In another embodiment, the benzathine salt has a characteristic XRP diffraction peak at a two-theta angle of approximately 8.0, 11.5, 16.0, 17.5, or 23.4°. In yet another embodiment, the crystalline benzathine salt has a DSC thermogram substantially as shown in FIG. 13. In an alternative embodiment, the crystalline benzathine salt has an endotherm with a peak temperature of about 156° C. and an onset temperature of about 154° C.

In yet another embodiment, the amine is a monoamine. The monoamine salt of {4,6-bis(dimethylamino)-2-(4-(4-(trifluoromethyl)benzamido)benzyl)pyrimidin-5-yl}acetic acid comprises from about 0.5 to about 1.5, from about 0.75 to about 1.25, or about 1 molar equivalent(s) of the acid of Formula I for a molar equivalent of the monoamine.

In one group of the monoamine salts of this embodiment, the monoamine of the monoamine salts has a primary amino group. In another group of the monoamine salts, the monoamine has a secondary amino group. In yet another group of the monoamine salts, the monoamine has a tertiary amino group. In still another group of the monoamine salts, the monoamine has a quaternary ammonium group.

Figure 15:
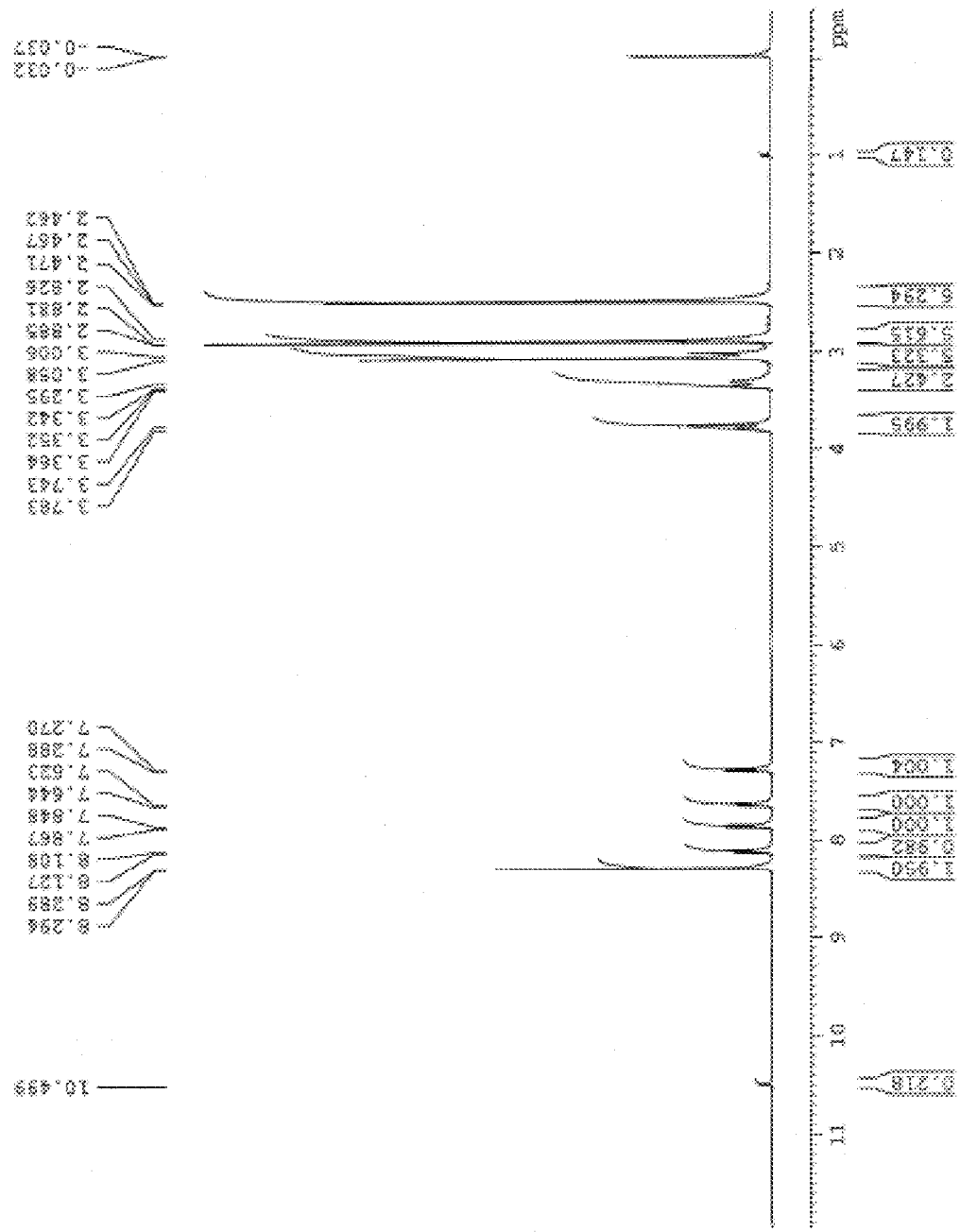
FIG. 15 depicts a $^1$H NMR spectrum of the crystalline choline salt of the acid of Formula I.

In an alternative embodiment, the amine is choline. The choline salt of {4,6-bis(dimethylamino)-2-(4-(4-(trifluoromethyl)benzamido)benzyl)pyrimidin-5-yl}acetic acid comprises about one molar equivalent of the acid of Formula I and about one molar equivalent of choline, as estimated based on its $^1$H NMR spectrum (FIG. 15).

Figure 16:
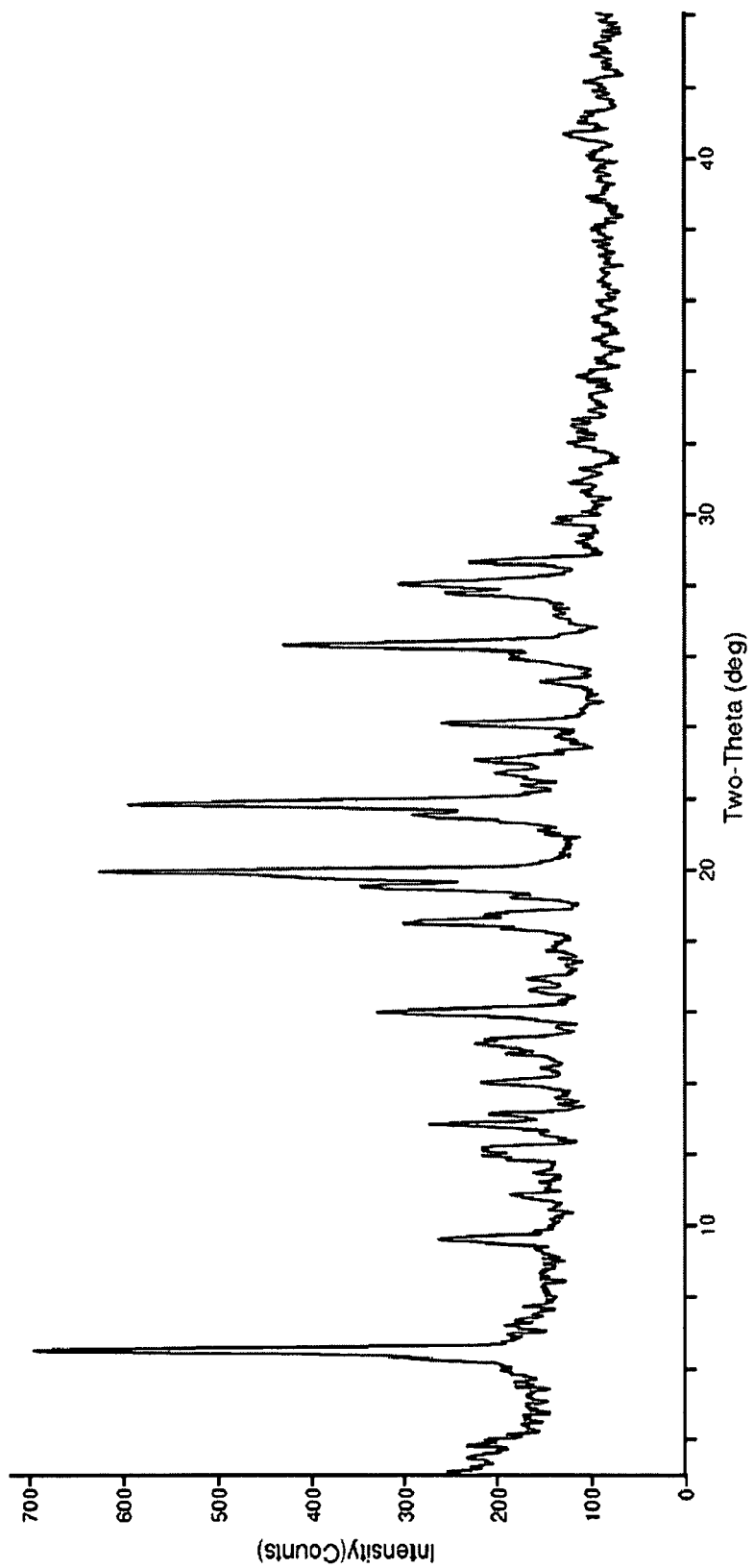
FIG. 16 depicts an XRP diffractogram of the crystalline choline salt of the acid of Formula I.
Figure 17:
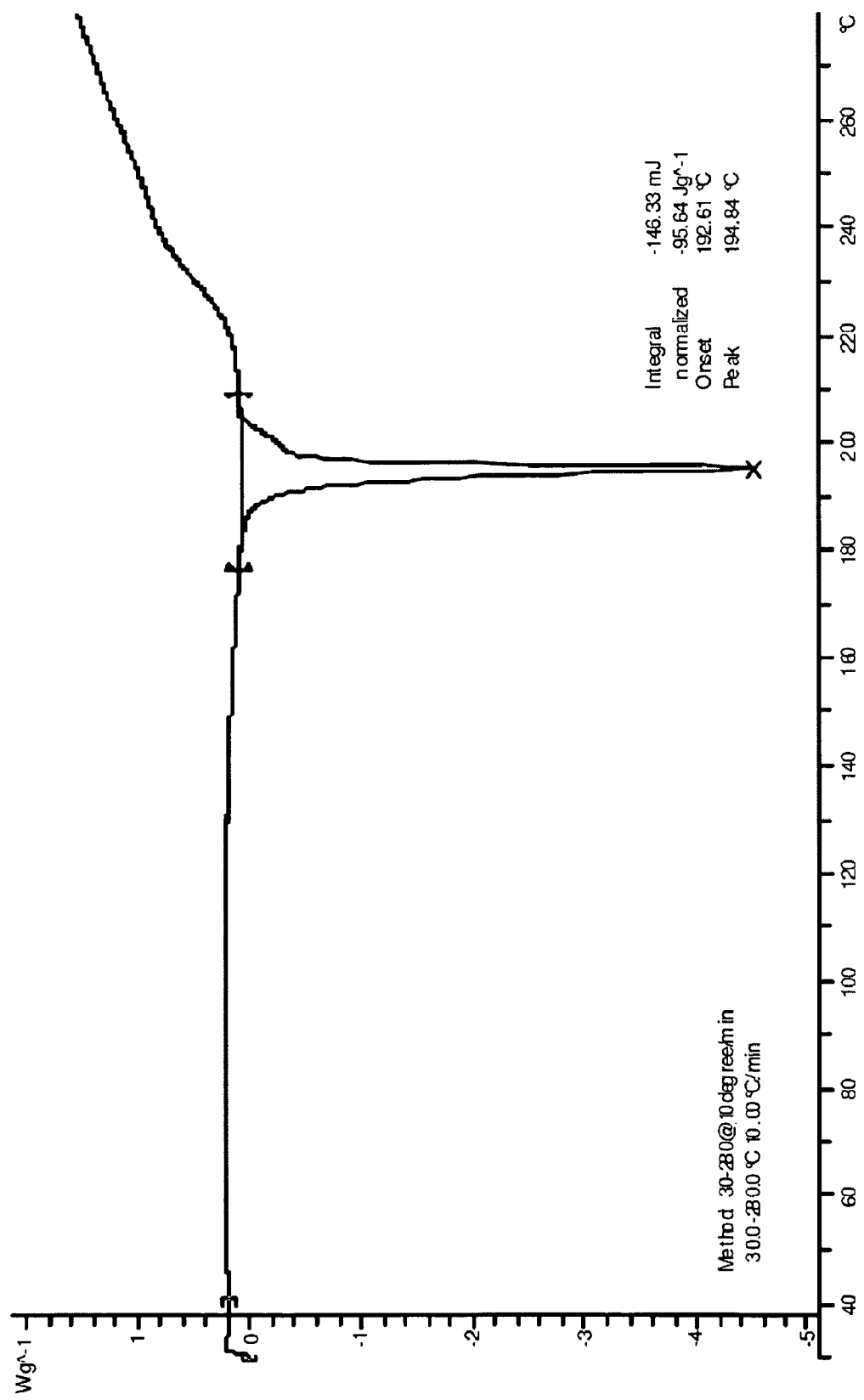
FIG. 17 depicts a DSC thermogram of the crystalline choline salt of the acid of Formula I.

In still another embodiment, the choline salt of the acid of Formula I is crystalline, which has an XRP diffraction pattern substantially as shown in FIG. 16. In one embodiment, the choline salt has characteristic XRP diffraction peaks at two-theta angles of approximately 6.5, 19.6, 20.0, 21.9, and 26.4°. In another embodiment, the choline salt has a characteristic XRP diffraction peak at a two-theta angle of approximately 6.5, 19.6, 20.0, 21.9, or 26.4°. In still another embodiment, the crystalline choline salt has a DSC thermogram substantially as shown in FIG. 17. In an alternative embodiment, the crystalline choline salt has an endotherm with a peak temperature of about 195° C. and an onset temperature of about 193° C.

It should be understood that the numerical values of the peaks of the X-ray powder diffraction patterns may vary slightly from one machine to another or from one sample to another, and so the values quoted are not to be construed as absolute, but with an allowable variability, such as 0.1°, which is recommended in the United State Pharmacopeia, 2007, 387-389.

Process of Preparation

Also provided is a process for preparing an amine salt of the acid of Formula (I). In one embodiment, the process comprises reacting {4,6-bis(dimethylamino)-2-(4-(4-(trifluoromethyl)benzamido)benzyl)pyrimidin-5-yl}acetic acid with an amine in a solvent at a first predetermined temperature. In another embodiment, the process further comprises precipitating the amine salt at a second predetermined temperature.

In an alternative embodiment, the process comprises the steps of: (a) generating an amine salt by reacting {4,6-bis(dimethylamino)-2-(4-(4-(trifluoromethyl)benzamido)-benzyl)pyrimidin-5-yl}acetic acid with an amine in a solvent at a first predetermined temperature; and (b) precipitating the amine salt at a second predetermined temperature.

Suitable solvents for use in preparing the amine salts of the acid of Formula I include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

In certain embodiments, the amine salt forming reaction (i.e., step a) is carried out at a temperature from about −10 to about 150° C., from about 10 to about 110° C., or from about 20 to about 100° C. In one embodiment, the solvent is acetonitrile, acetone, methyl ethyl ketone, methyl isobutyl ketone, N,N-dimethylformamide, dimethylsulfoxide, a low alkanol (e.g., methanol, ethanol, n-propanol, isopropanol, sec-butanol, or 2-methoxyethanol), methyl acetate, ethyl acetate, ethyl formate, isopropyl acetate, isobutyl acetate, chloroform, dichloromethane, methyl tert-butyl ether, tetrahydrofuran, 1,4-dioxane, petroleum ether, hexanes, heptane, toluene, water, or a mixture thereof. In another embodiment, the solvent is a low alkanol of 1 to 5 carbons, such as methanol, ethanol, propanol, isopropanol, sec-butanol, 2-methoxyethanol, or a mixture thereof.

In certain embodiments, the amine salt forming reaction is performed in the presence of an excess amount of the amine to maximize the yield of the reaction. The molar ratio of the amino group on the amine versus the acid of Formula I is no less than about 1.01, no less than about 1.05, no less than about 1.1, no less than about 1.2, from about 1.05 to about 10, from about 1.1 to about 5, or from about 1.2 to about 2.5.

In certain embodiments, the salt forming reaction is performed in a solution, that is, both the acid of Formula I and the amine are dissolved in the solvent. In certain embodiments, the salt forming reaction is performed as a slurry mixture of the acid of Formula I and the amine in the solvent. In this case, the acid of Formula I is not fully dissolved, whereas the amine is completely dissolved.

In certain embodiment, the amine salt formed in the amine forming reaction step may be precipitated out from the reaction solution or slurry mixture using conventional methods, including, but not limited to, cooling, chilling, solvent evaporation, addition of an anti-solvent, or reverse addition to an anti-solvent. The precipitating step may be carried out at a temperature from about −50 to about 100° C., from about −30 to about 50° C., or from about −10 to about 30° C. To accelerate the precipitation (crystallization) step, the process may further comprise the step of seeding the reaction solution or mixture. The process may also comprise an isolation step, in which the precipitate may be isolated by a conventional method, such as filtration and centrifugation, followed by washing with a solvent and then drying.

In one embodiment, the amine salt is prepared by (a) reacting {4,6-bis(dimethylamino)-2-(4-(4-(trifluoromethyl)-benzamido)benzyl)pyrimidin-5-yl}acetic acid with the amine in a low alkanol, such as ethanol, at an elevated temperature, to generate a clear reaction solution. When the amine is a diamine, the molar ratio of the diamine molecule versus the acid of Formula I, in the reaction solution, is no less than about 0.505, no less than about 0.525, no less than about 0.55, or no less than about 0.60; but no greater than about 10 or about 100. When the amine is a monoamine, the molar ratio of the monoamine molecule versus the acid of Formula I, in the reaction solution, is no less than about 1.01, no less than about 1.05, no less than about 1.1; but no greater than about 10 or about 100.

The amine salt may be precipitated by cooling the reaction solution to or below room temperature, or by solvent evaporation. The amine salt precipitates may also be formed by adding an anti-solvent to the reaction solution, or by adding the reaction solution to an anti-solvent.

Suitable anti-solvents include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane, 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including isopropanol, 1-propanol, 1-butanol, 2-butanol, t-butanol, 3-methyl-1-butanol, 1-pentanol, 2-ethoxyethanol, and ethyleneglycol; ethers, including diethyl ether, diisopropyl ether, methyl t-butyl ether, diphenyl ether, 1,2-dimethoxyethane, bi(2-methoxyethyl)ether, 1,1-dimethoxymethane, 2,2-dimethoxypropane, and anisole; ketones, including butanone, methyl isopropyl ketone, methyl butyl ketone, and methyl isobutyl ketone; esters, including methyl acetate, ethyl formate, ethyl acetate, propyl acetate, isopropyl acetate, isobutyl acetate, and butyl acetate; carbonates, including ethylene carbonate and propylene carbonate; nitro compounds, including nitromethane and nitrobenzene; heterocycles; carbon sulfide; water; and mixtures thereof.

When two solvents are used as a solvent/anti-solvent pair, the amine salt of the acid of Formula I has a higher solubility in the solvent than in the anti-solvent. Optionally, the solvent and the anti-solvent in a solvent/anti-solvent pair are at least partially miscible.

In another embodiment, the amine salt is prepared by (a) reacting a slurry of {4,6-bis(dimethylamino)-2-(4-(4-(trifluoromethyl)-benzamido)benzyl)pyrimidin-5-yl}acetic acid with the amine in a solvent, such as ethanol, at room temperature or an elevated temperature. After reaction, the amine salt may be recovered as solid by cooling, evaporating solvent from, or adding an anti-solvent to the slurry reaction mixture.

To accelerate the precipitation (crystallization) step, the process may further comprise the step of seeding the reaction solution or mixture, prior to or during the initiation of the precipitation step. The amount of seed crystals added exceeds the saturation amount in the solvent being used so that there are undissolved seed crystals present in the reaction solution.

Other salt forming methods may also be applicable in the present invention. For example, the amine salt of the acid of Formula I may be prepared by converting a salt of the acid, e.g., sodium salt or potassium salt, to an amine salt via cation exchange using a cation exchange column. The amine salt of the acid of Formula I may also be produced by physically grinding solid {4,6-bis(dimethylamino)-2-(4-(4-(trifluoromethyl)-benzamido)benzyl)pyrimidin-5-yl}acetic acid and the amine together in the absence of a solvent.

In addition to precipitation and crystallization, the solid amine salts provided herein may also be prepared using conventional methods known to those skilled in the art, including spray drying, roller drying, lyophilization, and melt crystallization.

Pharmaceutical Compositions

Also provided is a pharmaceutical composition which comprises an amine salt of {4,6-bis(dimethylamino)-2-(4-(4-(trifluoromethyl)benzamido)-benzyl)pyrimidin-5-yl}acetic acid, or a pharmaceutically acceptable hydrate or solvate thereof, as an active pharmaceutical ingredient, in combination with one or more pharmaceutically acceptable carriers or excipients. The choice of excipient, to a large extent, depends on factors, such as the particular mode of administration, the effect of the excipient on the solubility and stability of the active ingredient, and the nature of the dosage form.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The amine salts of the acid of Formula I provided herein may be administered alone, or in combination with one or more other compounds provided herein, one or more other active ingredients. The pharmaceutical compositions that comprise an amine salt provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy, supra; Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understand that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and $H_2$-receptor antagonists.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, crosslinked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including lard, benzoinated lard, olive oil, cottonseed oil, white petrolatum, and plastibase; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stiffing.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al. in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In another embodiment, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiment, the pharmaceutical compositions provided herein are formulated as ESC controlled-release dosage form, which comprises an osmotic membrane that coats a core comprising the active ingredient(s), hydroxyethyl cellulose, and other pharmaceutically acceptable excipients.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder or disease associated with CRTH2 and/or one or more other $PGD_2$ receptors by administering to a subject having or being suspected to have such a condition or disease, a therapeutically effective amount of an amine salt of {4,6-bis(dimethylamino)-2-(4-(4-(trifluoromethyl)benzamido)-benzyl)pyrimidin-5-yl}acetic acid, or a pharmaceutically acceptable hydrate or solvate thereof; or a pharmaceutical composition thereof.

In another embodiments, provided is a method of treating, preventing, or ameliorating one or more symptoms of a disease or disorder responsive to modulation of CRTH2 and/or one or more other $PGD_2$ receptors, comprising administering to a subject having or being suspected to have such a disease or disorder, a therapeutically effective amount of one or more of the amine salts or compositions provided herein.

In yet another embodiment, provided is a method of treating, preventing, or ameliorating one or more symptoms of a disease or disorder mediated by CRTH2 and/or one or more other $PGD_2$ receptors, comprising administering to a subject having or being suspected to have such a condition or disease, a therapeutically effective amount of one or more of the amine salts or compositions provided herein.

In yet another embodiment, provided is a method for treating, preventing, or ameliorating one or more symptoms of an eosinophil-related disease, comprising administering to a subject a therapeutically effective amount of an amine salt of {4,6-bis(dimethylamino)-2-(4-(4-(trifluoromethyl)benzamido)-benzyl)pyrimidin-5-yl}acetic acid, or a pharmaceutically acceptable hydrate or solvate thereof; or a pharmaceutical composition thereof.

In yet another embodiment, provided is a method for treating, preventing, or ameliorating one or more symptoms of a basophil-related disease, comprising administering to a subject a therapeutically effective amount of an amine salt of {4,6-bis(dimethylamino)-2-(4-(4-(trifluoromethyl)benzamido)-benzyl)pyrimidin-5-yl}acetic acid, or a pharmaceutically acceptable hydrate or solvate thereof; or a pharmaceutical composition thereof.

In still another embodiment, provided is a method for treating, preventing, or ameliorating one or more symptoms of an inflammatory disease, comprising administering to a subject a therapeutically effective amount of an amine salt of {4,6-bis(dimethylamino)-2-(4-(4-(trifluoromethyl)benzamido)-benzyl)pyrimidin-5-yl}acetic acid, or a pharmaceutically acceptable hydrate or solvate thereof; or a pharmaceutical composition thereof.

The disorders and diseases treatable with one or more of the amine salts provided herein include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, allergic rhinitis, otitis media, exercise induced asthma, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disease is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disease is asthma, exercise induced asthma, allergic rhinitis, atopic dermatitis, chronic obstructive plumonary disease, or allergic conjunctivitis.

In certain embodiments, the disease is Churg-Strauss syndrome or sinusitis.

Depending on the disease to be treated and the subject's condition, the amine salts or compositions provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable carriers, adjuvants and vehicles appropriate for each route of administration. Also provided is administration of the amine salts provided herein in a depot formulation, in which the active ingredient is released over a predefined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with CRTH2 and/or one or more other $PGD_2$ receptors, an appropriate dosage level generally is about 0.001 to 100 mg per kg patient body weight per day (mg/kg per day), about 0.01 to about 75 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day. In certain embodiments, the dosage level is about 0.01 to about 75 mg/kg per day. In certain embodiments, the dosage level is about 0.1 to about 50 mg/kg per day. In certain embodiments, the dosage level is about 0.5 to about 25 mg/kg per day. In certain embodiments, the dosage level is about 1 to about 20 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided is a method of modulating CRTH2 and/or one or more other $PGD_2$ receptors, comprising contacting the receptor(s) with one or more of the amine salts or compositions provided herein. In one embodiment, the receptor(s) are expressed by a cell.

The amine salts provided herein may also be combined or used in combination with other agents useful in the treatment, prevention, or amelioration of one or more symptoms of the diseases or conditions for which the amine salts provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, and those pathologies noted above.

Such other agents, or drugs, may be administered, by a route and in an amount commonly used therefor, simultaneously or sequentially with an amine salt provided herein. When an amine salt provided herein is used contemporaneously with one or more other drugs, a pharmaceutical composition containing such other drugs in addition to the amine salt provided herein may be utilized, but is not required. Accordingly, the pharmaceutical compositions provided herein include those that also contain one or more other active ingredients or therapeutic agents, in addition to an amine salt provided herein.

The weight ratio of the amine salt provided herein to the second active ingredient may be varied, and will depend upon the effective dose of each ingredient. Generally, an effective dose of each will be used. Thus, for example, when an amine salt provided herein is combined with a NSAID, the weight ratio of the amine salt provided herein to the NSAID may range from about 1,000:1 to about 1:1,000, or about 200:1 to about 1:200. Combinations of an amine provided herein and other active ingredients will generally also be within the aforementioned range, but in each case, an effective dose of each active ingredient should be used.

EXAMPLES

The amine salts of the acid of Formula I in the following examples were characterized with nuclear magnetic resonance spectroscopy (NMR), X-ray powder diffractometry (XRPD), differential scanning calorimetry (DSC), thermogravimetry (TGA), and scanning electron microscopy (SEM).

All $^1$H NMR spectra were recorded at 300 MHz on a Bruker Instruments NMR unless otherwise stated. Coupling constants (J) are in Hertz (Hz) and peaks are listed relative to TMS ($\delta$ 0.00 ppm).

X-ray powder diffraction data was recorded with a Rigaku MiniFlex X-ray powder diffractometer (Rigaku Americas, The Woodlands, Tex.). The radiation was CuKa (40 kV, 40 mA). Data were collected at room temperature from 3 to 45 degrees two-theta at 0.02 degrees per step and 0.6 sec per step. Samples were prepared on glass specimen holders as a thin layer of powdered material without solvent.

Differential scanning calorimetry was carried out using a Mettler 850, TA 2920. Samples were place in sealed aluminum pans for analysis with an empty aluminum pan as the reference. A heating rate of 10° C./min was employed over a temperature range from 30° C. to 280° C.

The thermogravimetric analysis was also conducted on a Mettler 850, TA 2920. Samples were placed into a ceramic or aluminum sample pan. A heating rate of 20° C./min was employed over a temperature range from 20° C. to 600° C.

The average particle size of the solid amine salts was determined using scanning electron microscopy.

Example 1

Base Selection for {4,6-Bis(dimethylamino)-2-(4-(4-(trifluoromethyl)benzamido)benzyl)pyrimidin-5-yl}Acetic Acid Salt The free acid of {4,6-bis(dimethylamino)-2-(4-(4-(trifluoromethyl)benzamido)-benzyl)pyrimidin-5-yl}acetic acid was screened with twenty two pharmaceutically acceptable bases and the results are summarized in Table 1, together with their aqueous solubility. Among the bases screened, ethylenediamine, piperazine, benzathine, and choline each produced crystalline solids suitable for pharmaceutical formulations and use as described herein.

Example 2

Figure 5:
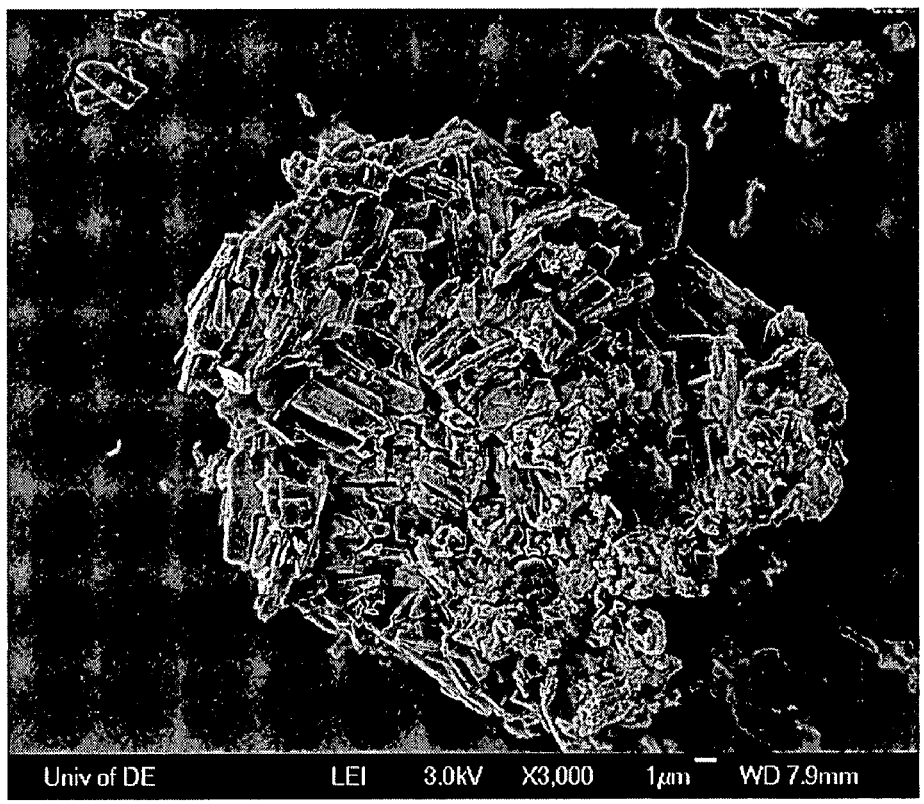
FIG. 5 depicts scanning electron microscopic (SEM) photographs of the crystalline ethylenediamine salt of the acid of Formula I.
Figure 5:
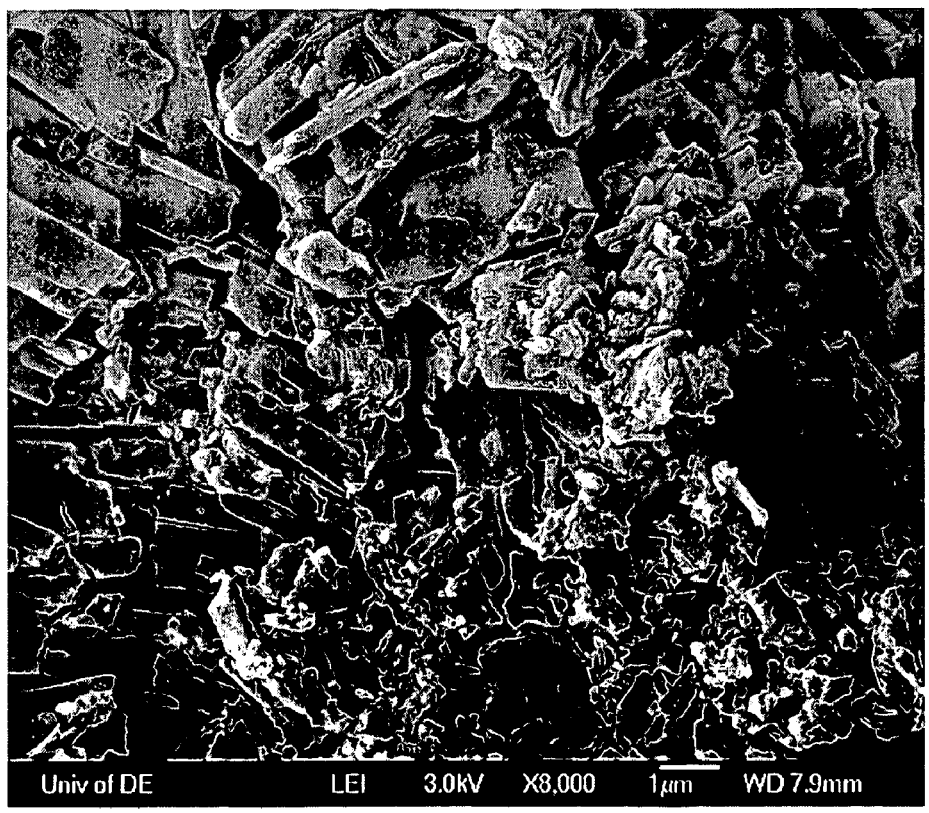

Preparation of an Ethylenediamine Salt of {4,6-Bis(dimethylamino)-2-(4-(4-(trifluoromethyl)benzamido)benzyl)pyrimidin-5-yl}Acetic Acid A mixture of {4,6-bis(dimethylamino)-2-(4-(4-(trifluoromethyl)benzamido)-benzyl)pyrimidin-5-yl}acetic acid (25.2 mg, 0.05 mmol) and ethylenediamine (1.68 mg, 0.03 mmol) in ethanol (1.1 mL) was heated at the reflux temperature to obtain a clear solution. The clear solution was then allowed to cool to room temperature and stirred for additional 2 hr. The precipitate was collected by filtration, washed with 0.5 mL of EtOH/Heptane (1:1, v/v), and dried at ambient temperature under vacuum to yield plate-like crystals (20.1 mg) (FIG. 5).

The stoichiometry of the ethanolamine salt was determined using $^1$H NMR (FIG. 1). The ethylenediamine salt of the acid of Formula I contains about two molar equivalents of the acid and one molar equivalent of ethylenediamine. For two molar equivalents of ethanol, there is about one molar equivalent of ethanol in the crystalline salt. The crystalline ethylenediamine salt contains about 4% of ethanol. The X-ray powder diffraction pattern of the ethylenediamine salt is illustrated in FIG. 2, having a characteristic XRP diffraction peak expressed in two-theta at 5.9°. This confirmed that the ethylenediamine salt is crystalline material.

The differential scanning calorimetric thermogram of the ethylenediamine salt is illustrated in FIG. 3. The ethylenediamine salt exhibits endotherms with a peak temperature of 123.1° C. and an onset temperature of 114.1° C., and a peak temperature of 216.0° C. and an onset temperature of 212.1° C.

TABLE 1

BASE SCREENING

| Base | Results | Aqueous Solubility at 25° C. (mg/mL) |
|---|---|---|
| Ethylenediamine | Crystalline solid | 5.8 |
| Piperazine | Crystalline solid | 5.4 |
| Benzathine | Crystalline solid | 0.08 |
| Choline | Crystalline solid | 24.0 |
| Sodium hydroxide | Poor solubility | |
| Potassium hydroxide | Poor solubility | |
| Calcium hydroxide | Poor solubility | |
| Diethanolamine | Soluble | |
| Ethanolamine | Soluble | |

TABLE 1-continued

BASE SCREENING

| Base | Results | Aqueous Solubility at 25° C. (mg/mL) |
|---|---|---|
| N-Methyl-D-glucamine | Poor crystalline salt | |
| 1-(2-Hydroxyethyl)-pyrrolidine | Soluble | |
| L-Lysine | Very little crystalline salt formed | |
| L-Arginine | Poor solubility | |
| Ammonia | Very little crystalline salt formed | |
| Deanol | Very little crystalline salt formed | |
| Diethylamine | Poor crystalline salt | |
| 2-(Diethylamino)-ethanol | Very little crystalline salt formed | |
| Pyrrole | Very little crystalline salt formed | |
| Magnesium hydroxide | Very little crystalline salt formed | |
| 4-(2-hydroxyethyl)-morpholine | Poor crystalline salt | |
| Triethanolamine | Very little crystalline salt formed | |
| Tromethamine | Poor crystalline salt | |

Figure 4:
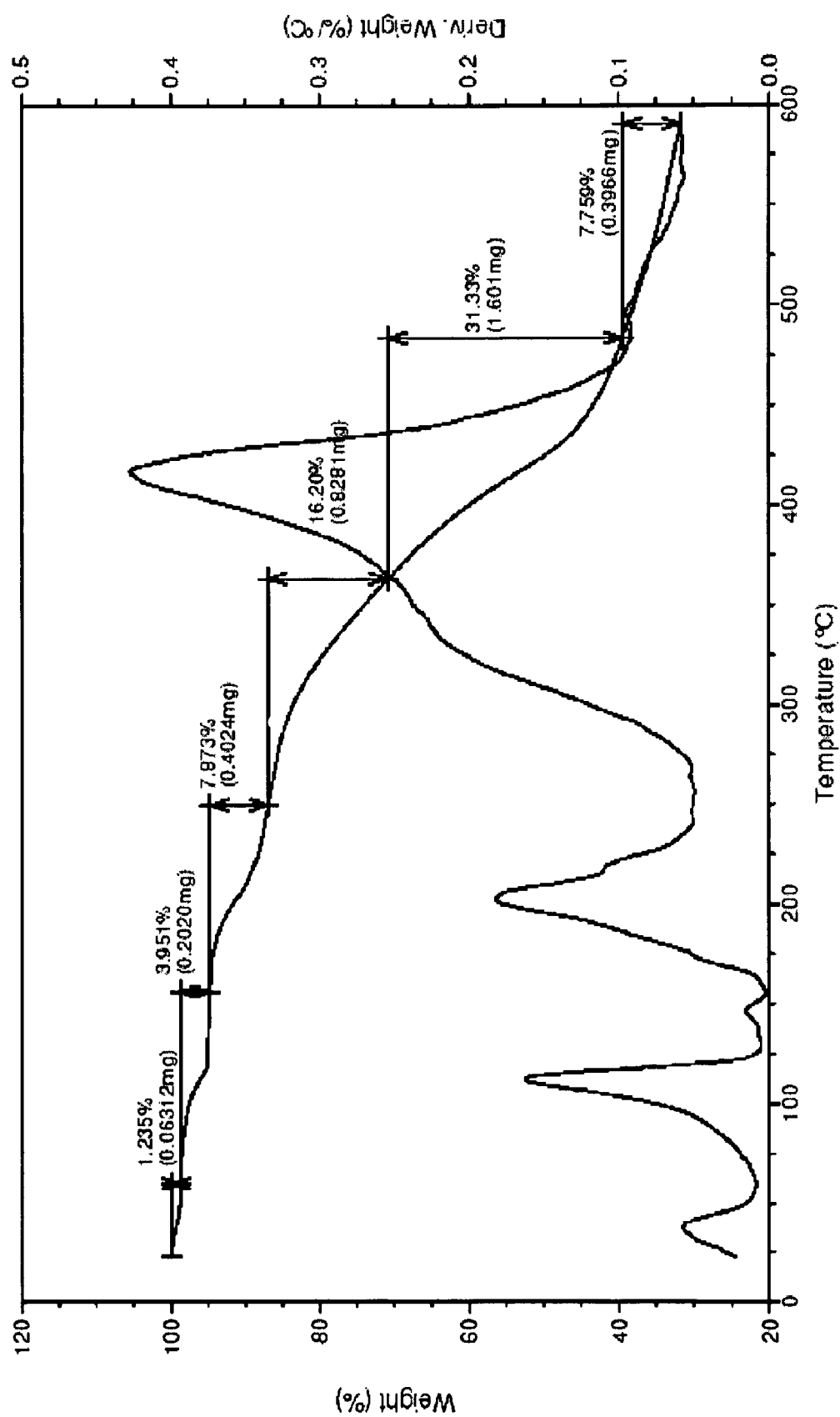
FIG. 4 depicts a thermogravimetric (TG) thermogram of the crystalline ethylenediamine salt of the acid of Formula I.

The thermogravimetric analysis thermogram is shown in FIG. 4. The ethylenediamine salt shows slight weight loss up to 75° C., and 3.951% weight loss between 125° C. to 150° C., which is consistent with the observation from the $^1$H NMR characterization (FIG. 1) that the crystalline ethylenediamine salt contains about 4% of ethanol.

Other solvent systems were also evaluated for producing a crystalline ethylenediamine salt of the acid of Formula I. The results are summarized in Table 2.

TABLE 2

SOLVENT SCREENING FOR THE ETHYLENEDIAMINE SALT

| Solvent System | Results |
|---|---|
| Methyl ethyl ketone (MEK) | Soluble solid |
| MeOH | Soluble solid |
| EtOH | Crystalline solid |
| Acetone | Insoluble solid |
| Methyl isobutyl ketone (MIBK) | Soluble solid |

Example 3

Figure 10:
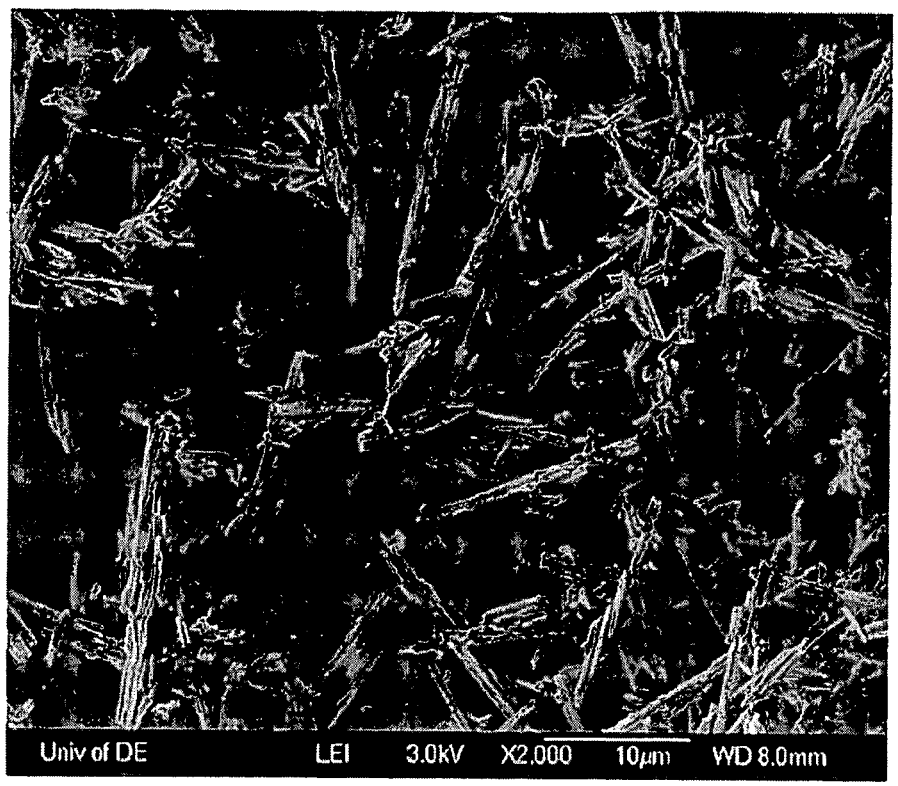
FIG. 10 depicts SEM photographs of the crystalline piperazine salt of the acid of Formula I.
Figure 10:
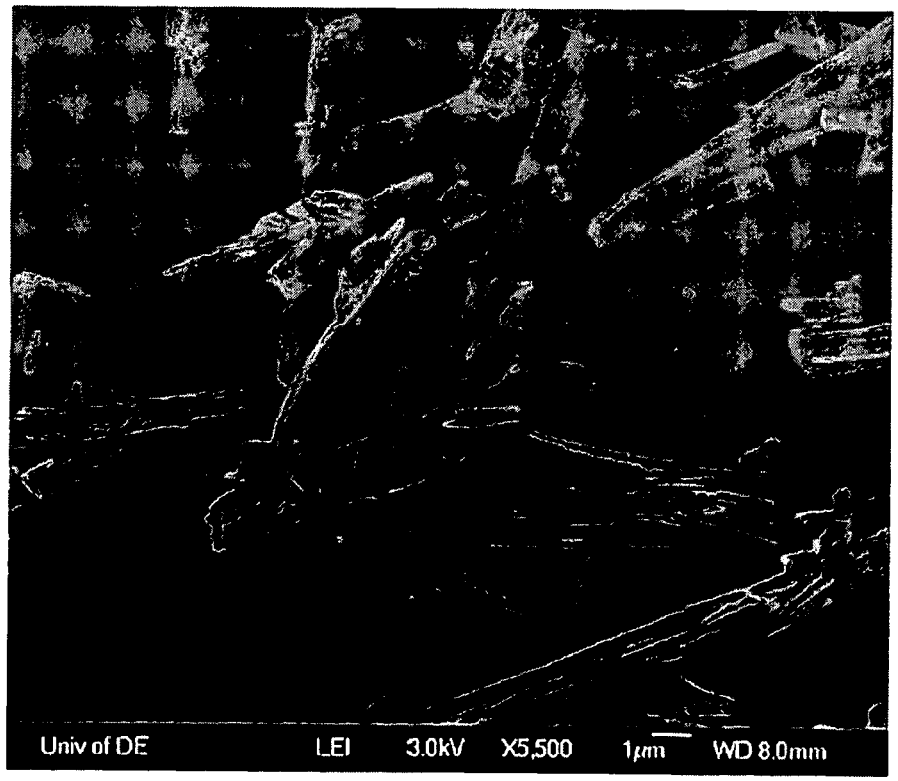

Preparation of an piperazine Salt of {4,6-Bis(dimethylamino)-2-(4-(4-(trifluoromethyl)benzamido)benzyl)pyrimidin-5-yl}Acetic Acid A mixture of {4,6-bis(dimethylamino)-2-(4-(4-(trifluoromethyl)benzamido)-benzyl)pyrimidin-5-yl}acetic acid (25.0 mg, 0.05 mmol) and piperazine (2.38 mg, 0.03 mmol) in ethanol (1.1 mL) was heated at the reflux temperature to obtain a clear solution. The clear solution was then allowed to cool to room temperature, and stirred for additional 2 hr. The precipitate was collected by filtration, washed with 0.5 mL of tert-butyl methyl ether (TBME), and dried at ambient temperature under vacuum to yield needle-like crystals (21.7 mg) (FIG. 10).

The stoichiometry of the piperazine salt was determined using $^1$H NMR (FIG. 6). The piperazine salt of the acid of Formula I contains about two molar equivalents of the acid and one molar equivalent of piperazine.

The X-ray powder diffraction pattern of the piperazine salt is illustrated in FIG. 7, having characteristic XRP diffraction peaks expressed in two-theta at: 10.7, 15.9, 22.3, and 24.0°. This confirmed that the piperazine salt is crystalline material.

The DSC thermogram of the piperazine salt is illustrated in FIG. 8. The piperazine salt exhibits a strong endotherm with a peak temperature of 223.2° C. and an onset temperature of 219.3° C., and a weak endotherm with a peak temperature of 202.6° C. and an onset temperature of 198.4° C.

Figure 9:
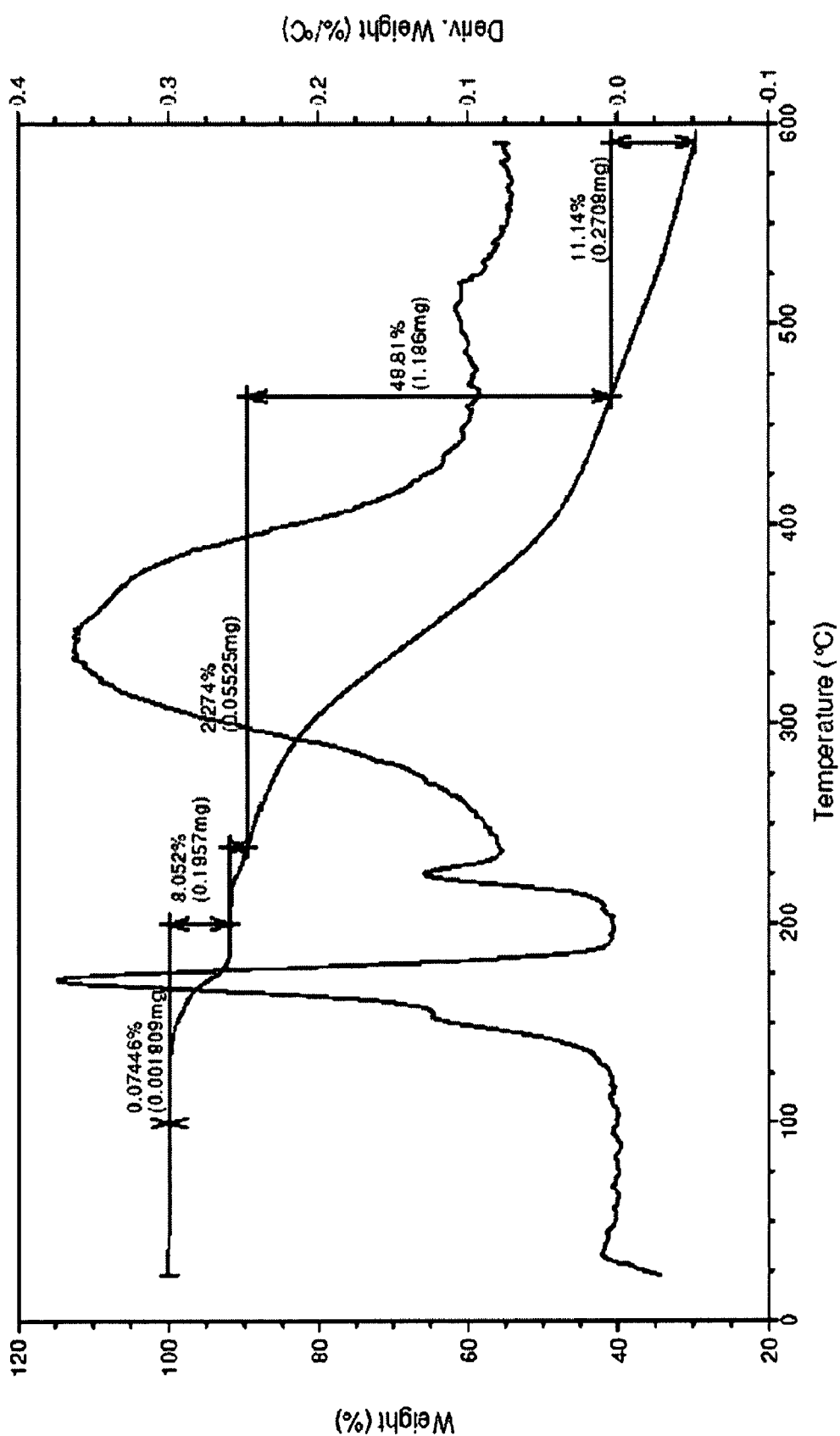
FIG. 9 depicts a TG thermogram of the crystalline piperazine salt of the acid of Formula I.

The thermogravimetric analysis thermogram of the piperazine salt is shown in FIG. 9. The ethylenediamine salt shows slight weight loss up to 75° C., and 3.951% weight loss between 125 to 150° C.

Other solvent systems were also evaluated for producing a crystalline piperazine salt of the acid of Formula I. The results are summarized in Table 3.

TABLE 3

SOLVENT SCREENING FOR THE PIPERAZINE SALT

| Solvent System | Results |
| --- | --- |
| EtOH | Crystalline solid |
| Acetone | Insoluble |
| THF | Crystalline solid |
| EtOH/H$_2$O | Crystalline solid |
| Methyl ethyl ketone (MEK) | Insoluble |
| Isopropanol (IPA) | Insoluble |
| Acetonitrile | Insoluble |

Example 4

Figure 14:
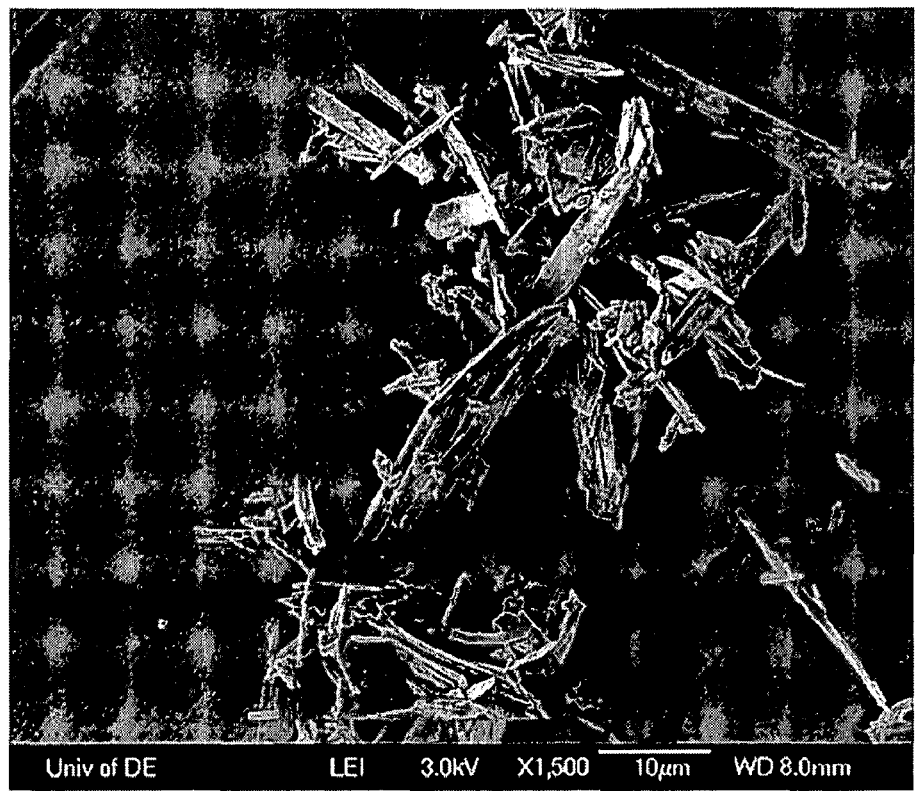
FIG. 14 depicts SEM photographs of the crystalline benzathine salt of the acid of Formula I.
Figure 14:
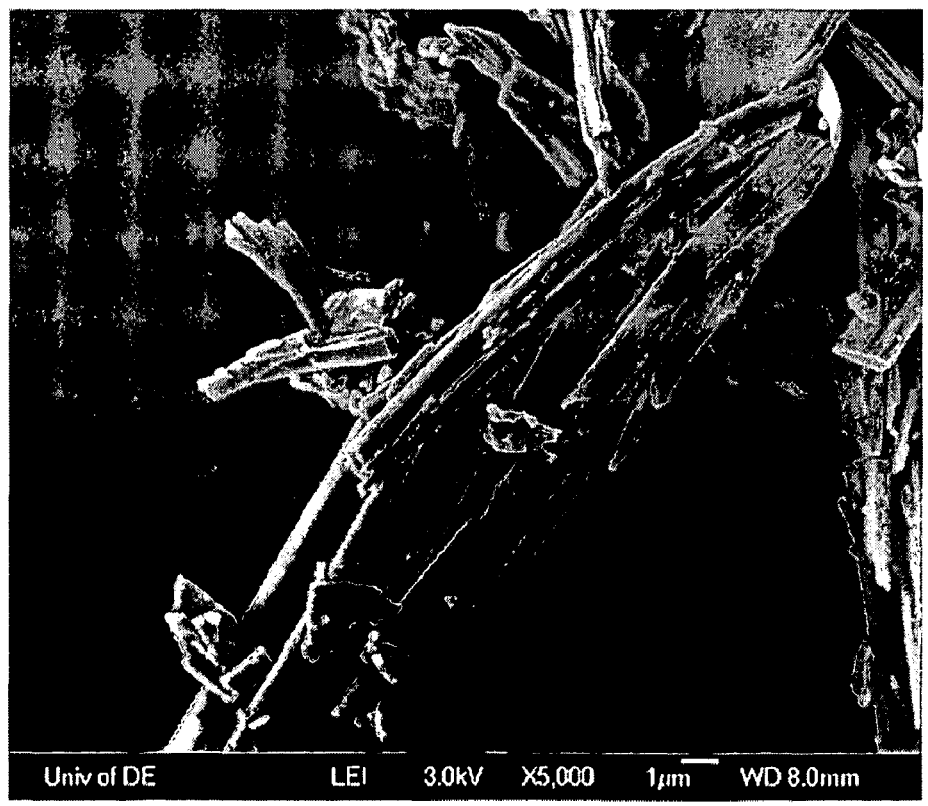

Preparation of a Benzathine Salt of {4,6-Bis(dimethylamino)-2-(4-(4-(trifluoromethyl)benzamido)benzyl)pyrimidin-5-yl}Acetic Acid A mixture of {4,6-bis(dimethylamino)-2-(4-(4-(trifluoromethyl)benzamido)-benzyl)pyrimidin-5-yl}acetic acid (250.0 mg, 0.5 mmol) and benzathine (134.4 mg, 0.56 mmol) in ethanol (3.0 mL) was heated at the reflux temperature to obtain a clear solution. The clear solution was then allowed to cool to room temperature, and stirred for additional 2 hr. The precipitate was collected by filtration, washed with 2 mL of IPA/Heptane (1:1, v/v), and dried under vacuum to yield a rod-like crystalline solid (256.8 mg) (FIG. 14).

The stoichiometry of the benzathine salt was determined using $^1$H NMR (FIG. 11). The benzathine salt of the acid of Formula I contains about two molar equivalents of the acid and one molar equivalent of benzathine.

The X-ray powder diffraction pattern of the benzathine salt is illustrated in FIG. 12, having characteristic XRP diffraction peaks expressed in two-theta at: 8.0, 11.5, 16.0, 17.5, and 23.4°. This confirmed that the benzathine salt is crystalline material.

The DSC thermogram of the benzathine salt is illustrated in FIG. 13. The benzathine salt exhibits a strong endotherm with a peak temperature of 155.8° C. and an onset temperature of 154.2° C.

Example 5

Figure 19:
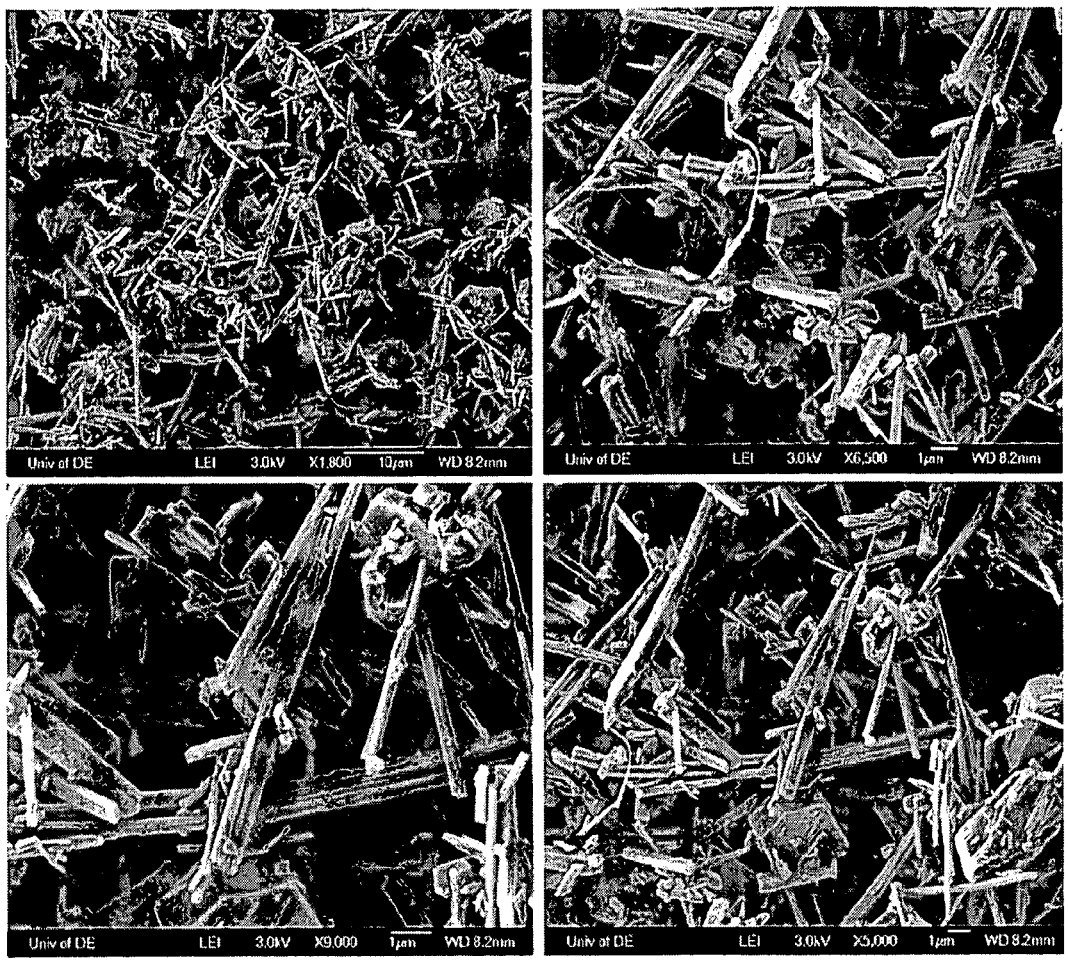
FIG. 19 depicts SEM photographs of the crystalline choline salt of the acid of Formula I.
Figure 20:
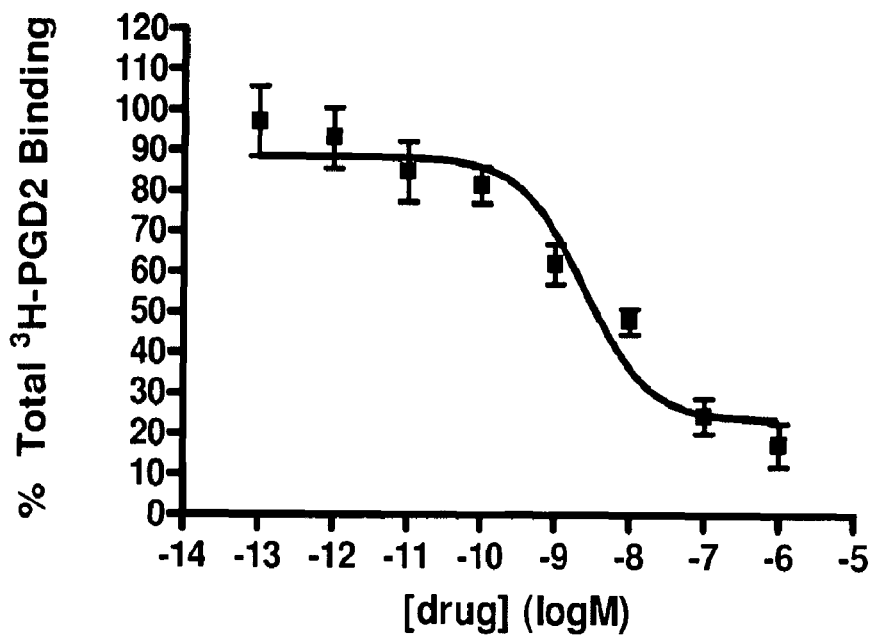
FIG. 20 depicts a dose response curve for {4,6-bis(dimethylamino)-2-(4-(4-(trifluoromethyl)-benzamido)benzyl)-pyrimidin-5-yl}acetic acid of Formula I in a competitive radioligand binding assay using CRTH2-transfected cells.
Figure 21:
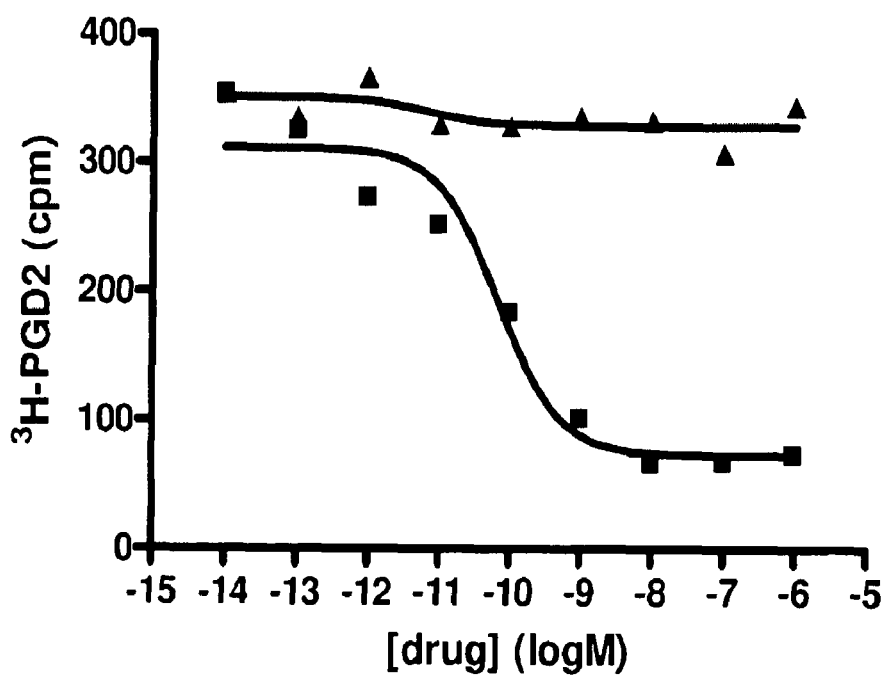
FIG. 21 depicts a dose response curve for {4,6-bis(dimethylamino)-2-(4-(4-(trifluoromethyl)-benzamido)benzyl)-pyrimidin-5-yl}acetic acid of Formula I (▲), along with a DP1-selective antagonist BWA 868C (■) for comparison, in a competitive radioligand binding assay using DP1-transfected cells.

Preparation of a Choline Salt of {4,6-Bis(dimethylamino)-2-(4-(4-(trifluoromethyl)benzamido)benzyl)pyrimidin-5-yl}Acetic Acid A mixture of {4,6-bis(dimethylamino)-2-(4-(4-(trifluoromethyl)benzamido)-benzyl)pyrimidin-5-yl}acetic acid (249.5 mg, 0.5 mmol) and choline (69.4 mg, 0.58 mmol) in IPA (3.5 mL) was heated at the reflux temperature to obtain a clear solution. The resulting clear solution was then allowed to cool to room temperature, and stirred for another 2 hr. The precipitate was collected by filtration, washed with 2 mL of IPA/Heptane (1:1, v/v), and dried at ambient temperature under vacuum to yield a rod-like and rhombs-like crystalline solid (232 mg) (FIG. 19).

The stoichiometry of the choline salt was determined using $^1$H NMR (FIG. 15). The choline salt of the acid of Formula I contains about one molar equivalent of the acid and one molar equivalent of choline.

The X-ray powder diffraction pattern of the choline salt is illustrated in FIG. 16, having a characteristic XRP diffraction peaks expressed in two-theta at: 6.5, 19.6, 20.0, 21.9, and 26.4°. This confirmed that the choline salt is crystalline material.

The DSC thermogram of the choline salt is illustrated in FIG. 17. The choline salt exhibits a strong endotherm with a peak temperature of 194.8° C. and an onset temperature of 192.6° C.

Figure 18:
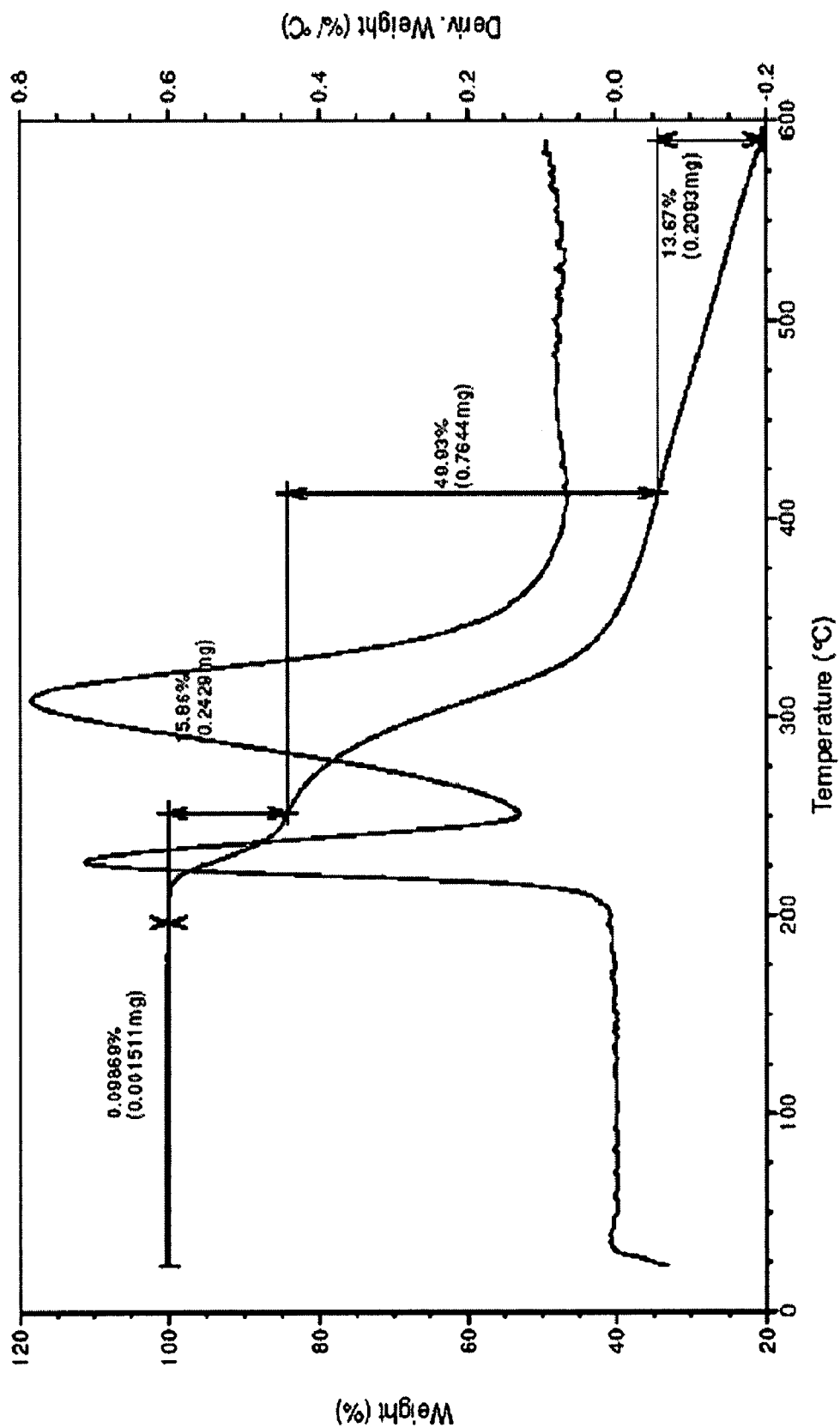
FIG. 18 depicts a TG thermogram of the crystalline choline salt of the acid of Formula I.

The thermogravimetric analysis thermogram of the choline salt is shown in FIG. 18. The choline salt shows nearly no weight loss up to 200° C.

Other solvent systems were also evaluated for producing a crystalline choline salt of the acid of Formula I. The results are summarized in Table 4.

TABLE 4

SOLVENT SCREENING FOR THE CHOLINE SALT

| Solvent System | Results |
| --- | --- |
| IPA/H$_2$O | Soluble solid |
| IPA | Crystalline solid |
| EtOH | Soluble solid |
| EtOH/H$_2$O | Soluble solid |

Example 6

Competitive Radioligand Binding Assay

The binding affinity and selectivity of the amine salts of 4,6-bis(dimethylamino)-2-(4-(4-(trifluoromethyl)benzamido)benzyl)pyrimidin-5-yl}acetic acid provided herein were evaluated using a competitive radioligand binding assay with stably-transfected cell lines expressing CRTH2 or DP1.

Prostaglandin D$_2$ and 13,14-dihydro-15-keto PGD$_2$ were obtained from Cayman Chemical (Ann Arbor, Mich.). Radiolabelled PGD$_2$ (5,6,8,9,12,14,15-$^3$H(N)) with a specific activity of 160 Ci/mmol was obtained from PerkinElmer (Boston, Mass.). Cell culture medium RPMI 1640, HEPES buffer, phosphate buffered saline (PBS), L-glutamine, and penicillin-streptomycin solution were obtained from Mediatech Inc. (Herndon, Va.). Fetal calf serum (FCS) was obtained from Cambrex (Walkersville, Md.). Puromycin was obtained from Invitrogen (San Diego, Calif.). Poly(ethyleneimine) (PEI) was obtained from Acros Organics (Morris Plains, N.J.). Purified monoclonal rat anti-human CRTH2 antibody (BM16), Rat IgG2a, κ, (clone R35-95), and goat anti-rat Ig-FITC were obtained from Becton Dickinson Biosciences (San Diego, Calif.). BSA (Fraction V) and sodium azide were obtained from Sigma Chemical Company (St. Louis).

The CRTH2 and DP1 stable cell lines were generated according to the procedure described by Sugimoto et al. (*J. Pharm. Exp. Therap.* 2003, 305, 347-352). These cell lines

What is claimed is:

1. A salt in a crystalline form, comprising ethylenediamine and {4,6-bis(dimethylamino)-2-(4-(4-(trifluoromethyl)benzamido)benzyl)pyrimidin-5-yl} acetic acid of Formula I:

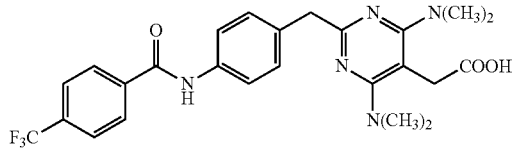

wherein the crystalline form has an X-ray powder diffraction pattern with a peak expressed in two-theta at approximately 5.9°, 11.6°, 17.5° and 29.4°.

2. The salt of claim 1, comprising of about two molar equivalents of the acid of Formula I and about one molar equivalent of ethylenediamine.

3. The salt of claim 1, having an X-ray powder diffraction pattern substantially as shown in FIG. 2.

4. The salt of claim 1, having a differential scanning calorimetric thermogram substantially as shown in FIG. 3.

5. The salt of claim 1, having a DSC thermogram with an endotherm at a peak temperature of about 123° C. and an onset temperature of about 114° C.

6. The salt of claim 1, having a DSC thermogram with an endotherm at a peak temperature of about 216° C. and an onset temperature of about 212° C.

7. The salt of claim 1, having an aqueous solubility of about 6 mg/mL at 25° C.

8. A salt in a crystalline form, comprising piperazine and {4,6-bis(dimethylamino)-2-(4-(4-(trifluoromethyl)benzamido)benzyl)pyrimidin-5-yl}acetic acid of Formula I:

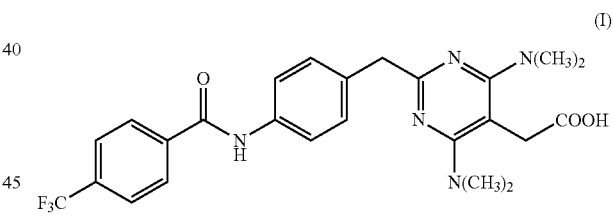

wherein the crystalline form has an X-ray powder diffraction pattern with a peak expressed in two-theta at approximately 10.7, 15.9, 22.3, or 24.0°.

9. The salt of claim 8, comprising of about two molar equivalents of the acid of Formula I and about one molar equivalent of piperazine.

10. The salt of claim 8, having an X-ray powder diffraction pattern substantially as shown in FIG. 7.

11. The salt of claim 8, having a differential scanning calorimetric thermogram substantially as shown in FIG. 8.

12. The salt of claim 8, having a DSC thermogram with an endotherm at a peak temperature of about 203° C. and an onset temperature of about 198° C.

13. The salt of claim 8, having a DSC thermogram with an endotherm at a peak temperature of about 223° C. and an onset temperature of about 219° C.

14. The salt of claim 8, having an aqueous solubility of about 5 mg/mL at 25° C.

15. A salt in a crystalline form, comprising benzathine and {4,6-bis(dimethylamino)-2-(4-(4-(trifluoromethyl)benzamido)benzyl)pyrimidin-5-yl}acetic acid of Formula I:

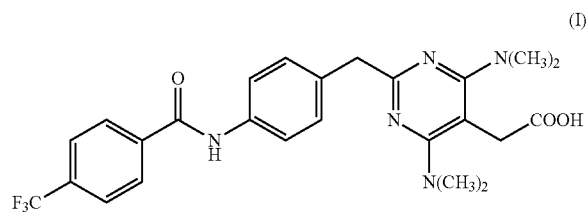

(I)

wherein the crystalline form has an X-ray powder diffraction pattern with a peak expressed in two-theta at approximately 8.0, 11.5, 16.0, 17.5, or 23.4°.

16. The salt of claim 15, comprising of about two molar equivalents of the acid of Formula I and about one molar equivalent of benzathine.

17. The salt of claim 15, having an X-ray powder diffraction pattern substantially as shown in FIG. 12.

18. The salt of claim 15, having a differential scanning calorimetric thermogram substantially as shown in FIG. 13.

19. The salt of claim 15, having a DSC thermogram with an endotherm at a peak temperature of about 156° C. and an onset temperature of about 154° C.

20. The salt of claim 15, having an aqueous solubility of about 0.08 mg/mL at 25° C.

21. A salt in a crystalline form, comprising choline and {4,6-bis(dimethylamino)-2-(4-(4-(trifluoromethyl)benzamido)benzyl)pyrimidin-5-yl}acetic acid of Formula I:

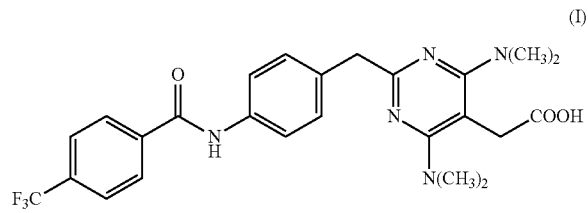

(I)

wherein the crystalline form has an X-ray powder diffraction pattern with a peak expressed in two-theta at approximately 6.5, 19.6, 20.0, 21.9, or 26.1°.

22. The salt of claim 21, comprising of about one molar equivalent of the acid of Formula I and about one molar equivalent of choline.

23. The salt of claim 21, having an X-ray powder diffraction pattern substantially as shown in FIG. 16.

24. The salt of claim 21, having a differential scanning calorimetric thermogram substantially as shown in FIG. 17.

25. The salt of claim 21, having a DSC thermogram with an endotherm at a peak temperature of about 195° C. and an onset temperature of about 193° C.

26. The salt of claim 21, having an aqueous solubility of about 24 mg/mL at 25° C.

27. A pharmaceutical composition comprising the salt of claim 1, and a pharmaceutically acceptable carrier or excipient.

28. The pharmaceutical composition of claim 27, wherein the composition is formulated for oral, nasal, bronchial, or topical administration.

29. The pharmaceutical composition of claim 27, wherein the composition is formulated as a single dosage form.

30. A process for the preparation of the salt of claim 1, comprising reacting {4,6-bis(dimethylamino)-2-(4-(4-(trifluoromethyl)benzamido)benzyl)-pyrimidin-5-yl}acetic acid with the amine in a solvent at a first predetermined temperature.

31. The process of claim 30, further comprising precipitating the salt at a second predetermined temperature.

32. A process for the preparation of the salt of claim 1, comprising the steps of:
(a) generating the amine salt by reacting {4,6-bis(dimethylamino)-2-(4-(4-(trifluoromethyl)benzamido)benzyl)pyrimidin-5-yl}acetic acid with the amine in a solvent at a first predetermined temperature; and
(b) precipitating the amine salt at a second predetermined temperature.

33. The process of claim 30, wherein the first temperature is from about −10 to about 150° C.

34. The process of claim 30, wherein the first temperature is from about 20 to 100° C.

35. The process of claim 31, wherein the second temperature is from about −50 to 50° C.

36. The process of claim 31, wherein the second temperature is from about −23 to 35° C.

37. The process of claim 30, wherein the solvent is selected from the group consisting of methanol, ethanol, isopropanol, propanol, tetrahydrofuran, water, and mixtures thereof.

38. The process of claim 30, wherein an anti-solvent is added in the precipitating step to effect precipitation.

39. The process of claim 38, wherein the anti-solvent is selected from the group consisting of water, alkanes, ethers, aromatic hydrocarbons, and mixtures thereof.

* * * * *